US011486993B2

(12) United States Patent
Habib

(10) Patent No.: US 11,486,993 B2
(45) Date of Patent: Nov. 1, 2022

(54) RESONANCE BASED DISTANCE ESTIMATION AND IDENTIFICATION

(71) Applicant: Honda Motor Co., Ltd., Tokyo (JP)

(72) Inventor: Ahsan Habib, Kirkland, WA (US)

(73) Assignee: HONDA MOTOR CO., LTD., Tokyo (JP)

(*) Notice: Subject to any disclaimer, the term of this patent is extended or adjusted under 35 U.S.C. 154(b) by 670 days.

(21) Appl. No.: 16/407,993

(22) Filed: May 9, 2019

(65) Prior Publication Data

US 2020/0249338 A1 Aug. 6, 2020
US 2021/0364618 A9 Nov. 25, 2021

Related U.S. Application Data

(60) Provisional application No. 62/799,541, filed on Jan. 31, 2019.

(51) Int. Cl.
*G01S 13/28* (2006.01)
*H04W 4/46* (2018.01)
(Continued)

(52) U.S. Cl.
CPC .......... *G01S 13/288* (2013.01); *A61B 5/0036* (2018.08); *A61B 5/0042* (2013.01);
(Continued)

(58) Field of Classification Search
CPC ...... G01S 13/931; G01S 13/84; G01S 13/003; G01S 13/288; G01S 7/4865; G01S 2013/9325; H04W 4/46
(Continued)

(56) References Cited

U.S. PATENT DOCUMENTS 3,152,326 A * 10/1964 Merlo ................... G01S 13/931
  367/96
3,176,294 A *  3/1965 Merlo ..................... G01S 13/62
  342/71
(Continued)

FOREIGN PATENT DOCUMENTS

DE       10161507 A1 *  7/2003 ............. G01S 13/84
DE  102015105161 A1 * 10/2015 ............. G01S 17/36
(Continued)

OTHER PUBLICATIONS

Md. Ahsan Habib and Tasbirun Nahian Upal, "A novel methodology for indoor positioning," World Congress on Nature and Biolgoically Inspired Computing (NABIC 2009), Coimbatore, India, Dec. 9, 2009.

*Primary Examiner* — Erin F Heard
*Assistant Examiner* — Michael W Justice
(74) *Attorney, Agent, or Firm* — Rankin, Hill & Clark LLP

(57) ABSTRACT

A system for estimating a distance between vehicles may include an oscillator, a transmitter, a receiver, a summing circuit, a signal analyzer, a tunable phase shifter, a distance estimator, and/or a vehicle identifier. The oscillator may generate a generated oscillating signal, transmitted by the transmitter. The receiver may receive a processed signal derived by a system of a second vehicle. The summing circuit may add the generated oscillating signal to the received signal to produce the updated oscillating signal. The signal analyzer may detect a spike in amplitude associated with the updated oscillating signal. The tunable phase shifter may shift a phase of the generated oscillating signal by an incremental phase shift amount until a spike in amplitude is detected. The distance estimator may estimate the distance between the first vehicle and the second vehicle (Continued)

based on a total phase shift amount and the predetermined wavelength.

18 Claims, 17 Drawing Sheets

(51) Int. Cl.
| | | |
|---|---|---|
| *A61B 5/00* | (2006.01) | |
| *A61B 5/055* | (2006.01) | |
| *A61N 7/00* | (2006.01) | |
| *G01R 33/48* | (2006.01) | |
| *G01R 33/563* | (2006.01) | |
| *G01S 13/931* | (2020.01) | |
| *G05D 1/00* | (2006.01) | |

(52) U.S. Cl.
CPC ............... *A61B 5/055* (2013.01); *A61N 7/00* (2013.01); *G01R 33/4806* (2013.01); *G01R 33/4814* (2013.01); *G01R 33/5635* (2013.01); *G01S 13/931* (2013.01); *G05D 1/0027* (2013.01); *H04W 4/46* (2018.02); *G01S 2013/9325* (2013.01)

(58) Field of Classification Search
USPC .................. 342/70, 457, 125, 127, 442, 118
See application file for complete search history.

(56) References Cited

U.S. PATENT DOCUMENTS

| | | | | |
|---|---|---|---|---|
| 3,243,812 A * | 3/1966 | Williams | ................ | G01S 13/84 |
| | | | | 342/126 |
| 3,308,380 A * | 3/1967 | Graves | ................... | G01S 13/84 |
| | | | | 342/126 |
| 3,577,144 A * | 5/1971 | Girault | ................... | G01S 17/36 |
| | | | | 342/127 |
| 3,641,573 A * | 2/1972 | Albanese | ............. | G01S 13/325 |
| | | | | 342/131 |
| 3,691,559 A | 9/1972 | Jackson | | |
| RE28,302 E | 1/1975 | Staras et al. | | |
| 3,984,835 A * | 10/1976 | Kaplan | ................... | G01S 13/84 |
| | | | | 342/44 |
| 4,063,237 A | 12/1977 | Nier et al. | | |
| 4,167,737 A * | 9/1979 | Freedman | ............ | G01S 13/288 |
| | | | | 342/201 |
| 4,396,916 A * | 8/1983 | Schnerk | ................ | G01S 13/325 |
| | | | | 331/10 |
| 4,757,315 A | 7/1988 | Lichtenberg et al. | | |
| 4,833,480 A * | 5/1989 | Palmer | .................... | G01S 13/46 |
| | | | | 342/127 |
| 4,928,130 A * | 5/1990 | Pfabe | .................... | H01Q 15/14 |
| | | | | 342/9 |
| 5,311,271 A * | 5/1994 | Hurt | ........................ | G01S 17/36 |
| | | | | 356/5.1 |
| 6,492,933 B1 * | 12/2002 | McEwan | ............... | G01S 13/582 |
| | | | | 342/134 |
| 6,614,239 B2 | 9/2003 | Borghi | | |
| 6,856,281 B2 * | 2/2005 | Billington | ............. | G01S 13/583 |
| | | | | 342/174 |
| 7,095,362 B2 * | 8/2006 | Hoetzel | ................. | G01S 13/931 |
| | | | | 342/84 |
| 7,292,189 B2 | 11/2007 | Orr et al. | | |
| 7,466,219 B2 | 12/2008 | Ishimura et al. | | |
| 7,639,178 B1 | 12/2009 | Mulbrook et al. | | |
| 7,791,528 B2 * | 9/2010 | Klotzbuecher | ....... | G01S 13/584 |
| | | | | 342/132 |
| 8,255,144 B2 * | 8/2012 | Breed | ..................... | G01S 17/86 |
| | | | | 340/436 |
| 8,798,907 B2 * | 8/2014 | Shida | .................... | G01S 5/0072 |
| | | | | 701/301 |
| 8,965,301 B2 | 2/2015 | Kluge et al. | | |
| 9,751,506 B2 * | 9/2017 | Mudalige | ............... | G08G 1/166 |
| 9,915,725 B1 | 3/2018 | Charvat et al. | | |
| 10,042,365 B2 * | 8/2018 | Switkes | ................. | G08G 1/167 |
| 10,185,329 B2 * | 1/2019 | Giles | .................... | B60W 10/18 |
| 10,732,645 B2 * | 8/2020 | Switkes | ................. | G08G 1/166 |
| 2003/0102997 A1 * | 6/2003 | Levin | .................... | G01S 13/931 |
| | | | | 340/902 |
| 2004/0196177 A1 * | 10/2004 | Billington | ............. | G01S 13/583 |
| | | | | 342/174 |
| 2010/0127915 A1 * | 5/2010 | Klotzbuecher | .......... | G01S 7/35 |
| | | | | 342/112 |
| 2011/0273324 A1 * | 11/2011 | Petillon | ................. | G01S 13/878 |
| | | | | 367/127 |
| 2018/0081029 A1 | 3/2018 | Davis et al. | | |
| 2018/0113476 A1 * | 4/2018 | Giles | .................... | G05D 1/0295 |
| 2020/0358178 A1 * | 11/2020 | Nagaishi | ................ | G01S 7/4008 |

FOREIGN PATENT DOCUMENTS

| | | | | |
|---|---|---|---|---|
| DE | 102017221643 A1 * | 7/2018 | ............. | B60T 13/66 |
| WO | WO-03052455 A1 * | 6/2003 | ............. | G01S 13/84 |

* cited by examiner

RESONANCE BASED DISTANCE ESTIMATION AND IDENTIFICATION

CROSS-REFERENCE TO RELATED APPLICATIONS

This application claims the benefit of U.S. Provisional Patent Application, Ser. No. 62/799,541 entitled RESONANCE BASED DISTANCE ESTIMATION AND IDENTIFICATION, filed on Jan. 31, 2019; the entirety of the above-noted application(s) is incorporated by reference herein.

BACKGROUND

Often, a remote vehicle (RV) may be linked to a host vehicle (HV). Together, the HV and the RV may perform one or more cooperative tasks. For example, the HV may operate the RV in an autonomous fashion using vehicle to vehicle (V2V) communications. In any event, a distance between a center of the HV and a center of the RV may be a desired measurement, known as a relative distance between the HV and the RV. Different types of sensors may be implemented, such as a camera, radar, or light detection and ranging (LIDAR) sensors. However, each type of sensor may be associated with different types of drawbacks. Cameras may be susceptible to adverse weather conditions, radar may return false positives, and LIDAR sensors may be expensive or costly to implement. Further, these sensors all implement the principle of 'time of flight' (ToF), which requires a direct line of sight (LoS) between objects being measured.

BRIEF DESCRIPTION

According to one aspect, a system for estimating a distance between vehicles may include an oscillator, a transmitter, a receiver, a summing circuit, a signal analyzer, a tunable phase shifter, and a distance estimator. The oscillator may be equipped on a first vehicle and may generate a generated oscillating signal associated with a first phase and a predetermined wavelength. The transmitter may transmit the generated oscillating signal, an updated generated oscillating signal, or a modulated signal derived from the generated oscillating signal or the updated generated oscillating signal as a broadcasted signal. The receiver may receive a processed signal associated with a second phase as a received signal. The processed signal may be derived by a system of a second vehicle based on the broadcasted signal. The summing circuit may add the generated oscillating signal to the received signal or a demodulated signal derived from the received signal and produce the updated oscillating signal. The signal analyzer may detect a spike in amplitude associated with the updated oscillating signal. The tunable phase shifter may shift the first phase of the generated oscillating signal by an incremental phase shift amount when no spike in amplitude is detected. The distance estimator may estimate the distance between the first vehicle and the second vehicle based on a total phase shift amount and the predetermined wavelength when the spike in amplitude is detected.

The transmitter may modulate the generated oscillating signal to generate the modulated signal. The transmitter may modulate a frequency, an amplitude, or a phase of the generated oscillating signal to generate the modulated signal. The predetermined wavelength may be set based on a vehicle to vehicle (V2V) communication range distance between the first vehicle and the second vehicle or set as double the V2V communication range distance. The distance estimator may calculate the distance x between the first vehicle and the second vehicle as $x=((\pi-\varphi)\lambda)/2\pi$, wherein $\lambda$ is the predetermined wavelength set as double the V2V communication range distance between the first vehicle and the second vehicle, and wherein $\varphi$ is the total phase shift amount resulting in the spike in amplitude of the updated oscillating signal. The transmitter or receiver may include an omni-directional radio frequency (RF) antenna or a rotating directional RF antenna. The oscillator may generate the generated oscillating signal at a frequency less than 5 MHz and the modulated signal may have a frequency greater than 2 GHz.

The first vehicle may be a host vehicle and the second vehicle may be a remote vehicle and the host vehicle may direct an aspect of autonomous driving for the remote vehicle. The second vehicle may be a host vehicle and the first vehicle may be a remote vehicle and the host vehicle may direct an aspect of autonomous driving for the remote vehicle. The transmitter and the receiver may be mounted at a center area of the first vehicle. The signal analyzer may detect the spike in amplitude based on an amplitude of the updated oscillating signal exceeding a threshold amplitude. The tunable phase shifter may shift the first phase of the generated oscillating signal by decrementing the first phase by the incremental phase shift amount.

The predetermined wavelength may be set as double a vehicle to vehicle (V2V) communication range distance between the first vehicle and the second vehicle and the signal analyzer may detect the spike in amplitude of the updated oscillating signal when a phase shifted image of the first vehicle is one half the predetermined wavelength distance away from the second vehicle. The signal analyzer may detect the spike in amplitude based on an occurrence of resonance. The system for estimating the distance between vehicles may include a memory storing the distance between the first vehicle and the second vehicle when the spike in amplitude is detected.

According to one aspect, a method for estimating a distance between vehicles may include generating, at a first vehicle, a generated oscillating signal associated with a first phase and a predetermined wavelength, transmitting the generated oscillating signal, an updated generated oscillating signal, or a modulated signal derived from the generated oscillating signal or the updated generated oscillating signal as a broadcasted signal, receiving a processed signal associated with a second phase as a received signal, wherein the processed signal is derived by a system of a second vehicle based on the broadcasted signal, summing the generated oscillating signal with the received signal or a demodulated signal derived from the received signal and producing the updated oscillating signal, detecting a spike in amplitude associated with the updated oscillating signal, shifting the first phase of the generated oscillating signal by an incremental phase shift amount when no spike in amplitude is detected, and estimating the distance between the first vehicle and the second vehicle based on a total phase shift amount and the predetermined wavelength when the spike in amplitude is detected.

The method for estimating the distance between vehicles may include modulating the generated oscillating signal to generate the modulated signal. The method for estimating the distance between vehicles may include setting the predetermined wavelength based on a vehicle to vehicle (V2V) communication range distance between the first vehicle and the second vehicle or double the V2V communication range distance. The method for estimating the distance between vehicles may include calculating the distance x between the first vehicle and the second vehicle as $x=((\pi-\varphi)\lambda)/2\pi$, wherein $\lambda$ is the predetermined wavelength set as double the V2V communication range distance between the first vehicle and the second vehicle, and wherein $\varphi$ is the total phase shift amount resulting in the spike in amplitude of the updated oscillating signal.

According to one aspect, a system for confirming an identity of a remote vehicle among remote vehicles associated with a host vehicle may include an oscillator, a transmitter, a receiver, a tunable phase shifter, a signal analyzer, and a vehicle identifier. The oscillator may be equipped on a first vehicle. The oscillator may generate a first generated oscillating signal associated with a first phase and a second generated oscillating signal associated with the first phase. The transmitter may transmit the first generated oscillating signal to a first remote vehicle and a first test signal associated with a phase shift amount and a first time and the second generated oscillating signal to a second remote vehicle. The receiver may receive a first processed signal associated with the first phase and a second processed signal associated with the first phase. The tunable phase shifter may shift the first phase of the first generated oscillating signal by the phase shift amount at the first time. The signal analyzer may detect a spike in amplitude associated with one of the first processed signal or the second processed signal and no spike in amplitude associated with the other of the first processed signal and the second processed signal. The vehicle identifier may identify the first remote vehicle or the second remote vehicle based on detecting no spike in amplitude with the corresponding first processed signal or second processed signal.

DETAILED DESCRIPTION

Figure 1:
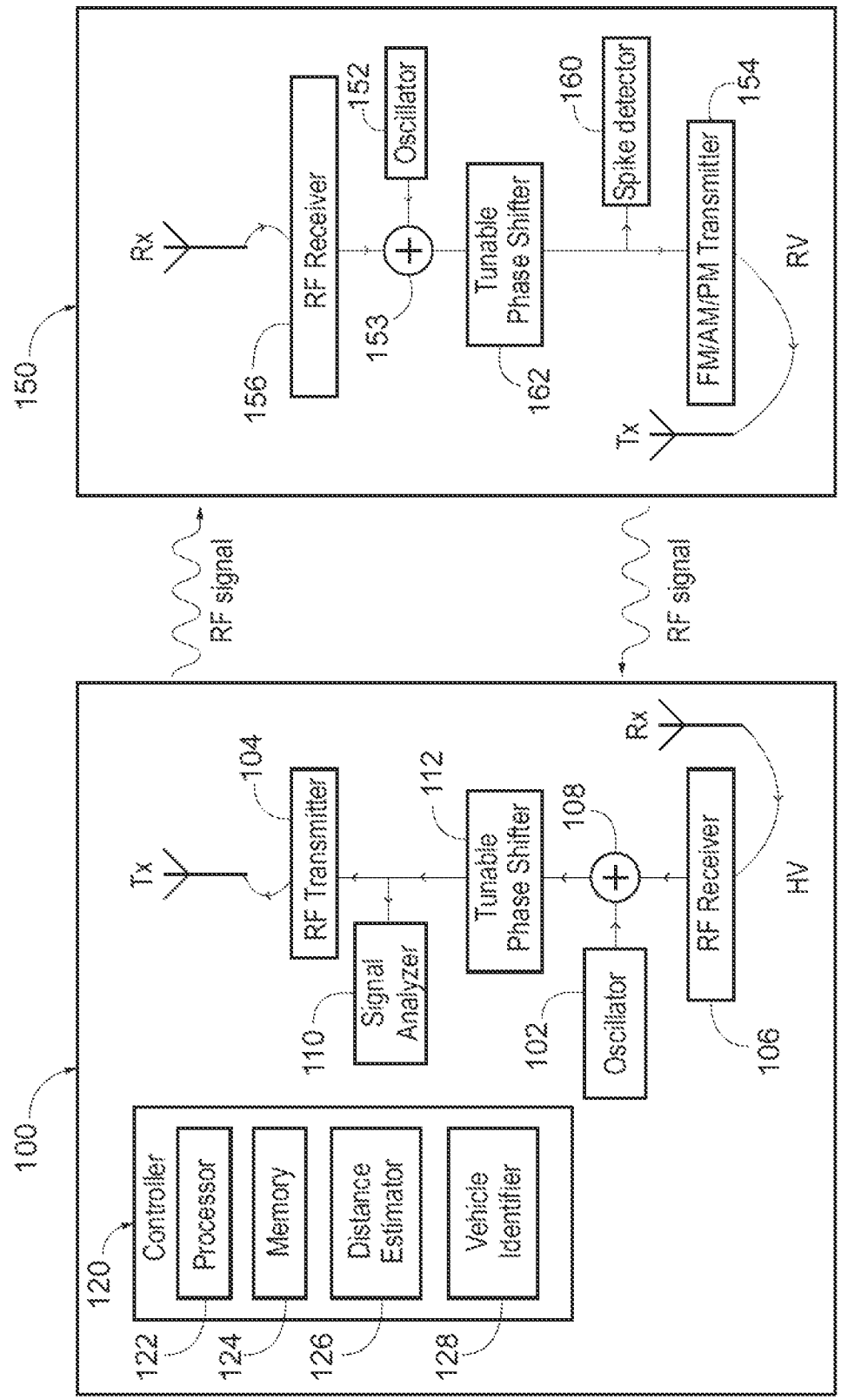
FIG. 1 is an exemplary component diagram of a system for estimating a distance between vehicles or system for confirming an identity of a remote vehicle among remote vehicles associated with a host vehicle, according to one aspect.

The following terms are used throughout the disclosure, the definitions of which are provided herein to assist in understanding one or more aspects of the disclosure.

A "processor", as used herein, processes signals and performs general computing and arithmetic functions. Signals processed by the processor may include digital signals, data signals, computer instructions, processor instructions, messages, a bit, a bit stream, or other means that may be received, transmitted, and/or detected. Generally, the processor may be a variety of various processors including multiple single and multicore processors and co-processors and other multiple single and multicore processor and co-processor architectures. The processor may include various modules to execute various functions.

A "memory", as used herein, may include volatile memory and/or non-volatile memory. Non-volatile memory may include, for example, ROM (read only memory), PROM (programmable read only memory), EPROM (erasable PROM), and EEPROM (electrically erasable PROM). Volatile memory may include, for example, RAM (random access memory), synchronous RAM (SRAM), dynamic RAM (DRAM), synchronous DRAM (SDRAM), double data rate SDRAM (DDRSDRAM), and direct RAM bus RAM (DRRAM). The memory may store an operating system that controls or allocates resources of a computing device.

A "bus", as used herein, refers to an interconnected architecture that is operably connected to other computer components inside a computer or between computers. The bus may transfer data between the computer components. The bus may be a memory bus, a memory controller, a peripheral bus, an external bus, a crossbar switch, and/or a local bus, among others. The bus may also be a vehicle bus that interconnects components inside a vehicle using protocols such as Media Oriented Systems Transport (MOST), Controller Area network (CAN), Local Interconnect Network (LIN), among others.

A "vehicle", as used herein, refers to any moving vehicle that is capable of carrying one or more human occupants and is powered by any form of energy. The term "vehicle" includes cars, trucks, vans, minivans, SUVs, motorcycles, scooters, boats, personal watercraft, and aircraft. In some scenarios, a motor vehicle includes one or more engines. Further, the term "vehicle" may refer to an electric vehicle (EV) that is powered entirely or partially by one or more electric motors powered by an electric battery. The EV may include battery electric vehicles (BEV) and plug-in hybrid electric vehicles (PHEV). Additionally, the term "vehicle" may refer to an autonomous vehicle and/or self-driving vehicle powered by any form of energy. The autonomous vehicle may or may not carry one or more human occupants. A host vehicle may manage one or more vehicle systems of a remote vehicle, including aspects related to autonomous operation.

A "vehicle system", as used herein, may be any automatic or manual systems that may be used to enhance the vehicle, driving, and/or safety. Exemplary vehicle systems include an autonomous driving system, an electronic stability control system, an anti-lock brake system, a brake assist system, an automatic brake prefill system, a low speed follow system, a cruise control system, a collision warning system, a collision mitigation braking system, an auto cruise control system, a lane departure warning system, a blind spot indicator system, a lane keep assist system, a navigation system, a transmission system, brake pedal systems, an electronic power steering system, visual devices (e.g., camera systems, proximity sensor systems), a climate control system, an electronic pretensioning system, a monitoring system, a passenger detection system, a vehicle suspension system, a vehicle seat configuration system, a vehicle cabin lighting system, an audio system, a sensory system, among others.

The aspects (e.g., vehicle identifiers, distance estimators, etc.) discussed herein may be described and implemented in the context of non-transitory computer-readable storage medium storing computer-executable instructions. Non-transitory computer-readable storage media include computer storage media and communication media. For example, flash memory drives, digital versatile discs (DVDs), compact discs (CDs), floppy disks, and tape cassettes. Non-transitory computer-readable storage media may include volatile and non-volatile, removable and non-removable media implemented in any method or technology for storage of information such as computer readable instructions, data structures, modules, or other data.

FIG. 1 is an exemplary component diagram of a system 100 for estimating a distance between vehicles or system 100 for confirming an identity of a remote vehicle among remote vehicles associated with a host vehicle, according to one aspect. The system 100 for estimating the distance between vehicles may include an oscillator 102, a transmitter 104, a receiver 106, a summing circuit 108, a signal analyzer 110, a tunable phase shifter 112, a controller 120 including a processor 122 and memory 124, a distance estimator 126, and a vehicle identifier 128.

According to one aspect, the system 100 for estimating the distance between vehicles may operate in a first mode, which may be a scanning mode where the system scans for other vehicles to estimate the distance between vehicles. In this regard, one of the vehicles may be a host vehicle (HV) and the other vehicle may be a remote vehicle (RV). With respect to the drawings described herein, the first vehicle may be the HV and the second vehicle may be the RV, although the opposite or other configurations may be possible (e.g., the first vehicle being the RV rather than the HV). The system 100 for estimating the distance between vehicles may operate on the principle of using radio frequency (RF) transmissions which are phase shifted to establish resonance with another vehicle, thereby providing RF resonance based range estimation between vehicles (e.g., a first vehicle and a second vehicle). The distance between the HV and the RV may be referred to as a relative distance between the two vehicles.

The oscillator 102 may be equipped on a first vehicle, which may be the HV, for example. The oscillator 102 may be a low frequency oscillator generating an oscillating signal less than 20 MHz. For example, the signal may be a generated oscillating signal associated with a first phase and a predetermined wavelength. This predetermined wavelength may be set based on a vehicle to vehicle (V2V) communication range distance between two vehicles (i.e., the HV and the RV or a first vehicle and a second vehicle). As will be appreciated from FIGS. 5-11, which will be described in greater detail herein, when the predetermined wavelength is set in this manner, resonance may occur when the phase shifted 'image' of the HV is 'virtually' located at a half predetermined wavelength distance from the RV being scanned. In this way, the resonance may be set to occur in a manner which assures occurrence within the V2V communication range distance. Specifically, according to one aspect, the predetermined wavelength may be set as double (or slightly less than double) the V2V communication range distance.

An output of the oscillator 102 generating the generated oscillating signal and the receiver 106 may be tied to the summing circuit 108. An output of the summing circuit 108 may be fed to the tunable phase shifter 112. The tunable phase shifter 112 may output its signal to the signal analyzer 110 and the transmitter 104.

The transmitter 104 may transmit the generated oscillating signal from the oscillator 102 to a system 150 of a second vehicle, which may also be a system for estimating a distance between vehicles. The summing circuit 108 may receive a signal from the oscillator 102 and from the receiver 106, summing these into an updated oscillating signal. The transmitter 104 may transmit the updated generated oscillating signal to the system 150 of the second vehicle.

Additionally, the transmitter 104 may perform modulation on a signal, such as frequency modulation, amplitude modulation, or phase modulation. In this regard, the transmitter 104 may modulate the generated oscillating signal or the updated generated oscillating signal to generate the modulated signal to be transmitted. Stated another way, the transmitter 104 may transmit the modulated signal, which is derived from the generated oscillating signal or the updated generated oscillating signal to the system 150 of the second vehicle. The signal transmitted by the transmitter 104 may be referred to as a broadcasted signal.

For example, the oscillator 102 may generate a 1.5 MHz signal (e.g., less than 5 MHz), which is a low frequency signal. As used herein, low frequency may refer to a signal in the 0.1 MHz to 25 MHz range. The transmitter 104, prior to transmitting this signal as the broadcasted signal, may modulate the frequency of the generated signal to be a high frequency, such as 2.4 GHz (greater than 2 GHz), for example. As used herein, high frequency may refer to a signal in the greater than 0.5 GHz range. This modulation may be performed to enable smaller sized antennas to be utilized for broadcasting and receiving the signals described herein.

The system 150 of the second vehicle may include one or more components which are similar or identical to the components of the system 100 for estimating the distance between vehicles. For example, the system 150 of the second vehicle may include a receiver 156, a tunable phase shifter 162, and a transmitter 154. Additionally, the system 150 of the second vehicle may include an oscillator 152, a signal analyzer 160, and a summing circuit 153.

The receiver 156 of the system 150 of the second vehicle may receive the broadcasted signal and demodulate the received signal. During the scanning mode, the oscillator 152, the summing circuit 153, the tunable phase shifter 162, and the signal analyzer 160 of the system 150 of the second vehicle are not required. The transmitter 154 of the system 150 of the second vehicle may transmit (e.g., pass along the received broadcasted signal) or re-transmit the broadcasted signal back to the system 100 for estimating the distance between vehicles of the first vehicle, which is the HV in this example.

In this way, the receiver 106 may receive a processed signal associated with a second phase as a received signal. If the system 150 of the second vehicle does not perform phase shifting using its own tunable phase shifter 162, the second phase may be equal to the first phase. However, in certain scenarios, the system 150 of the second vehicle may perform phase shifting, as will be described below, with reference to the system 100 for confirming the identity of the RV among RVs associated with the HV. In these scenarios, the second phase may not necessarily be equal to the first phase.

The receiver 106 may perform demodulation on a signal, such as frequency demodulation, amplitude demodulation, or phase demodulation. In this way, the receiver 106 may receive a processed signal associated with a second phase as a received signal and demodulate the received signal in a manner corresponding to the modulation performed prior to transmission of the broadcasted signal. As discussed, the processed signal may be derived by the system 150 of the second vehicle based on the broadcasted signal received by the system 150 of the second vehicle.

The transmitter 104, 154 and/or the receiver 106, 156 may include an omni-directional RF antenna or a rotating directional RF antenna. The omni-directional RF antenna may be utilized to provide range estimates or distance estimates between two vehicles, and the rotating directional RF antenna may provide range estimates or distance estimates between two vehicles as well as a directional measurement associated therewith in connection with the system 100 for confirming identities of vehicles. The transmitter 104, 154 and/or the receiver 106, 156 may be implemented as a transceiver or as separate devices and may transmit and/or receive frequency modulated (FM), amplitude modulated (AM), phase modulated, or pulse modulated signals. According to one aspect, the transmitter 104 and the receiver 106 may be mounted at a center portion or center area of the first vehicle, which may be either the HV or RV. Similarly, for the system 150 of the second vehicle, the transmitter 154 and the receiver 156 of that system may be mounted at a center portion or center area of the second vehicle, which may be the HV or RV.

The summing circuit 108 may, as previously discussed, sum the signals from the oscillator 102 and the receiver 106. In other words, the summing circuit 108 may add or combine the generated oscillating signal to the received signal or the demodulated signal derived from the received signal and produce the updated oscillating signal for transmission.

The signal analyzer 110 may be a circuit that monitors a signal and detects a spike in the monitored signal, such as via spike detection. The signal analyzer 110 may detect a spike in amplitude associated with the updated oscillating signal and provide an indication of when the spike occurs. Because the principle of resonance (and the setup of the summing circuit 108) is utilized, spikes occur when one vehicle is one half of the wavelength distance from another vehicle. Spikes may also occur due to a phase shift which causes one vehicle's phase shifted virtual position or virtual image to be the one half wavelength distance from the other vehicle. The signal analyzer 110 may be a spike detection circuit which detects the spike in amplitude based on an amplitude of the updated oscillating signal exceeding a threshold amplitude, due to an occurrence of resonance.

The tunable phase shifter 112 may shift the first phase of the generated oscillating signal by an incremental phase shift amount when no spike in amplitude is detected. The tunable phase shifter 112 may be a high precision tunable digital phase shifter. According to one aspect, the tunable phase shifter 112 may shift the first phase of the generated oscillating signal by decrementing the first phase by the incremental phase shift amount, and having the signal analyzer 110 check for the spike in amplitude. If no spike in amplitude is detected, then the image of the first vehicle (in the virtual, phase shifted sense) and the second vehicle are not positioned at the half predetermined wavelength distance from one another. In this regard, when no spike, and thus, no resonance is detected, the tunable phase shifter 112 may shift the phase of the generated oscillating signal by another incremental phase shift amount (e.g., 2× the incremental phase shift amount, then 3×, 4×, etc.).

When the predetermined wavelength is set as double the V2V communication range distance between the first vehicle and the second vehicle, resonance will occur when the 'virtual' distance between the phase shifted 'image' of the first vehicle is one half the predetermined wavelength distance away from the second vehicle. This may be seen with reference to FIGS. 5-11, described in greater detail herein.

The distance estimator 126 may estimate the distance between the first vehicle and the second vehicle based on a total phase shift amount and the predetermined wavelength when the spike in amplitude is detected (e.g., which is indicative of resonance). For example, the distance estimator 126 may calculate the distance x between the HV and the RV as $x=((\pi-\varphi)\lambda)/2\pi$, wherein $\lambda$ is the predetermined wavelength, which is set as double the V2V communication range distance between the HV and the RV, where $\varphi$ is the total phase shift amount resulting in the spike in amplitude of the updated oscillating signal. This distance x may be stored to the memory 124 of the system 100 for estimating the distance between vehicles in association with the spike in amplitude and utilized in associated with a tracking mode for the system 100 for estimating the distance between vehicles, as will be described below.

Although the system 100 for estimating the distance between vehicles, as described above, is implemented so that the HV performs the phase shifting of the signals, the RV may perform the phase shifting of the signals according to other aspects. Stated another way, according to one aspect, the first vehicle may be the HV and the second vehicle may be the RV. According to another aspect, the second vehicle may be the HV and the first vehicle may be the RV. In any event, the controller 120 of the HV may direct or control and aspect of autonomous driving (e.g., different vehicle systems) for the RV (e.g., based on the calculated estimated distance between the vehicles (first and second vehicle, HV and RV, etc.)).

Figure 2:
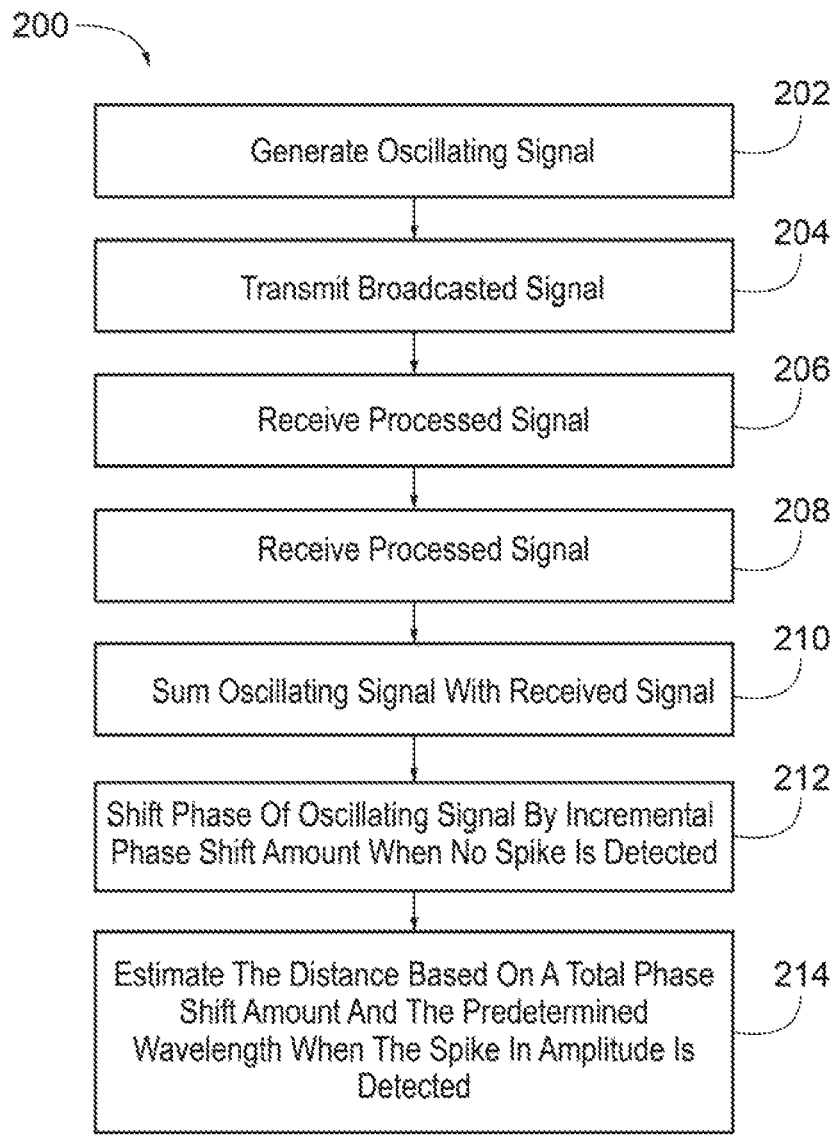
FIG. 2 is an exemplary flow diagram of a method for estimating a distance between vehicles, according to one aspect.

FIG. 2 is an exemplary flow diagram of a method 200 for estimating a distance between vehicles, according to one aspect, such as when operating in the scanning mode. The method may include generating 202, at a first vehicle, a generated oscillating signal associated with a first phase and a predetermined wavelength, transmitting 204 the generated oscillating signal, an updated generated oscillating signal, or a modulated signal derived from the generated oscillating signal or the updated generated oscillating signal as a broadcasted signal, receiving 206 a processed signal associated with a second phase as a received signal, wherein the processed signal is derived by the system of the second vehicle based on the broadcasted signal, summing 208 the generated oscillating signal with the received signal or a demodulated signal derived from the received signal and producing the updated oscillating signal, detecting 210 a spike in amplitude associated with the updated oscillating signal, shifting 212 the first phase of the generated oscillating signal by an incremental phase shift amount when no spike in amplitude is detected, and estimating 214 the distance between the first vehicle and the second vehicle based on a total phase shift amount and the predetermined wavelength when the spike in amplitude is detected.

Figures 3, 4:
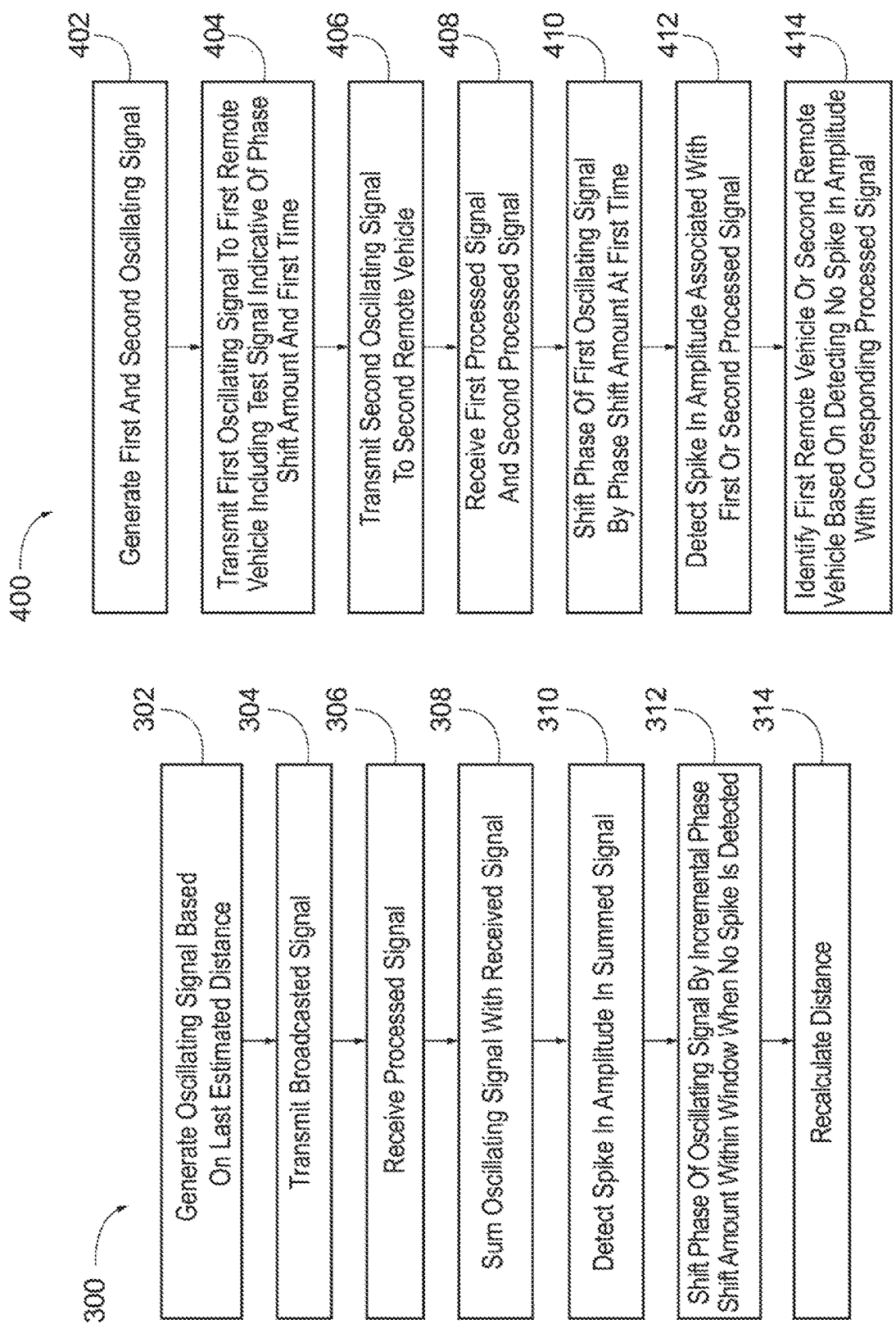
FIG. 3 is an exemplary flow diagram of a method for estimating a distance between vehicles, according to one aspect.
FIG. 4 is an exemplary flow diagram of a method for confirming an identity of a remote vehicle among remote vehicles associated with a host vehicle, according to one aspect.

FIG. 3 is an exemplary flow diagram of a method 300 for estimating a distance between vehicles, according to one aspect, such as when operating in the tracking mode. Based on the estimating the distance between the first vehicle and the second vehicle of the method 200, the method 300 may include generating 302 the oscillating signal based on the last estimated distance, transmitting 304 the generated oscillating signal, an updated generated oscillating signal, or a modulated signal derived from the generated oscillating signal or the updated generated oscillating signal as a broadcasted signal, receiving 306 a processed signal associated with a second phase as a received signal, wherein the processed signal is derived by the system of the second vehicle based on the broadcasted signal, summing 308 the generated oscillating signal with the received signal or a demodulated signal derived from the received signal and producing the updated oscillating signal, detecting 310 a spike in amplitude associated with the updated oscillating signal, shifting 312 the phase of the generated oscillating signal by an incremental or tracking phase shift amount when no spike in amplitude is detected and within a window to facilitate tracking of the second vehicle by incrementing or decrementing the tracking phase shift amount until the spike in amplitude is detected, and recalculating 314 or updating the distance between the first vehicle and the second vehicle based on an updated total phase shift amount (including the tracking phase shift amount which results in the spike in amplitude) and the predetermined wavelength when the spike in amplitude is detected.

FIG. 4 is an exemplary flow diagram of a method 400 for confirming an identity of a remote vehicle among remote vehicles associated with a host vehicle, according to one aspect, such as when operating in the confirmation of identity mode. The method 400 may include generating 402 a first generated oscillating signal associated with a first phase, generating a second generated oscillating signal associated with the first phase, transmitting 404 the first generated oscillating signal to a first remote vehicle and a first test signal associated with a phase shift amount and a first time, transmitting 406 the second generated oscillating signal to a second remote vehicle, receiving 408 a first processed signal associated with the first phase, receiving a second processed signal associated with the first phase, shifting 410 the first phase of the first generated oscillating signal by the phase shift amount at the first time, detecting 412 a spike in amplitude associated with one of the first processed signal or the second processed signal and no spike in amplitude associated with the other of the first processed signal and the second processed signal, and identifying 414 the first remote vehicle or the second remote vehicle based on detecting no spike in amplitude with the corresponding first processed signal or second processed signal.

FIGS. 5-11 are exemplary scenarios where the system 100 for estimating the distance between vehicles of FIG. 1 may be implemented, according to one aspect, when the system 100 for estimating the distance between vehicles is operating according to the scanning mode. FIGS. 5-11 are associated with different times (t-$t_6$) and corresponding phase shift amounts ($\varphi_i$ to $\varphi_i$*7).

Figure 5:
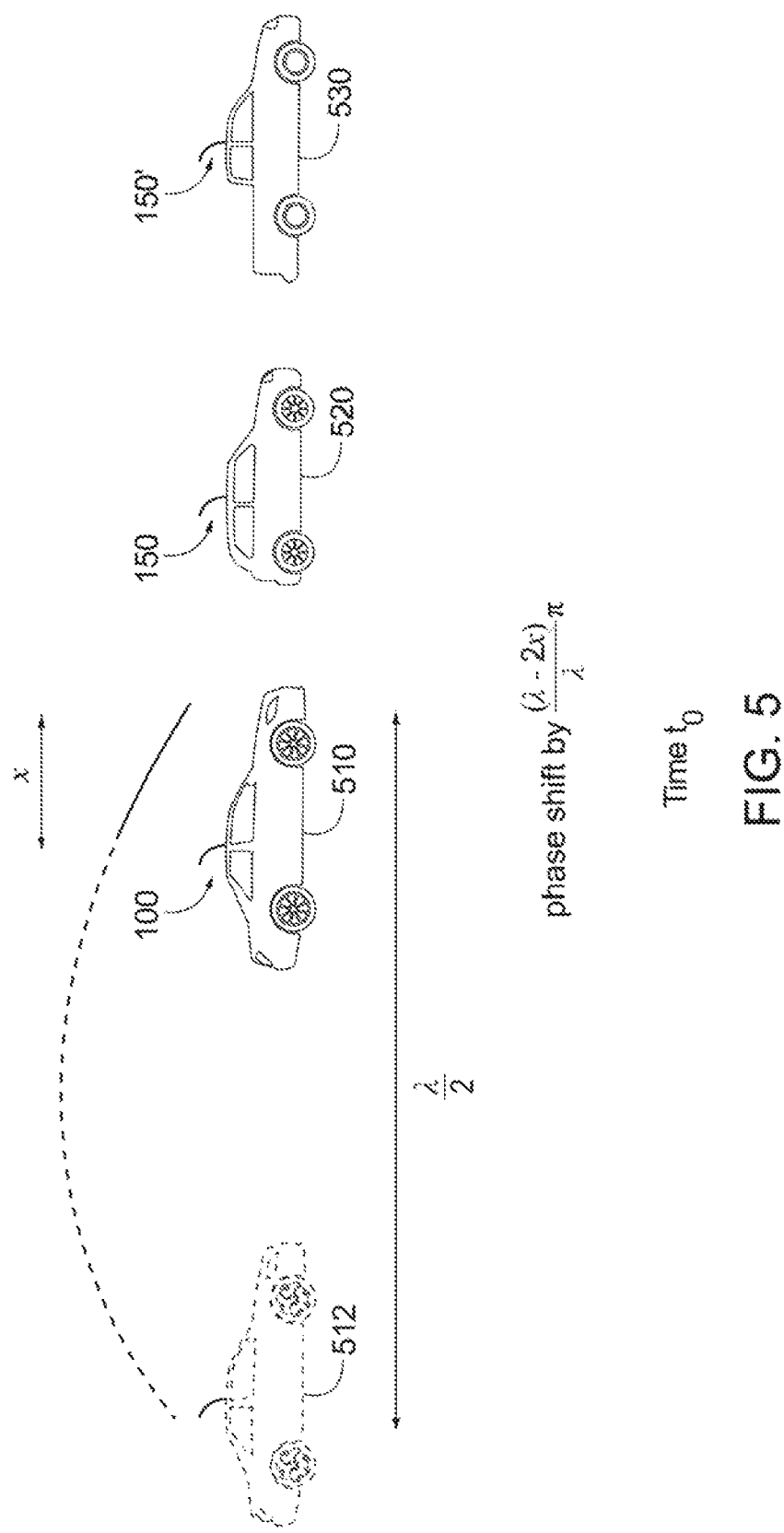
FIGS. 5-11 are exemplary scenarios where the system for estimating a distance between vehicles of FIG. 1 may be implemented, according to one aspect.

In FIG. 5, at time t, the tunable phase shifter 112 shifts the phase of the signal broadcast by the first vehicle 510 by $((\lambda-2x)\pi)/2\lambda$, where $\lambda$ is the predetermined wavelength, and x is a distance between phases, as seen in FIGS. 5-12. The signal analyzer 110 may check for a spike in the updated oscillating signal from a processed signal from a second vehicle 520. Because no resonance has occurred, the signal analyzer 110 will not detect any spike, and thus, the tunable phase shifter 112 will shift the phase of the signal incrementally.

Figure 6:
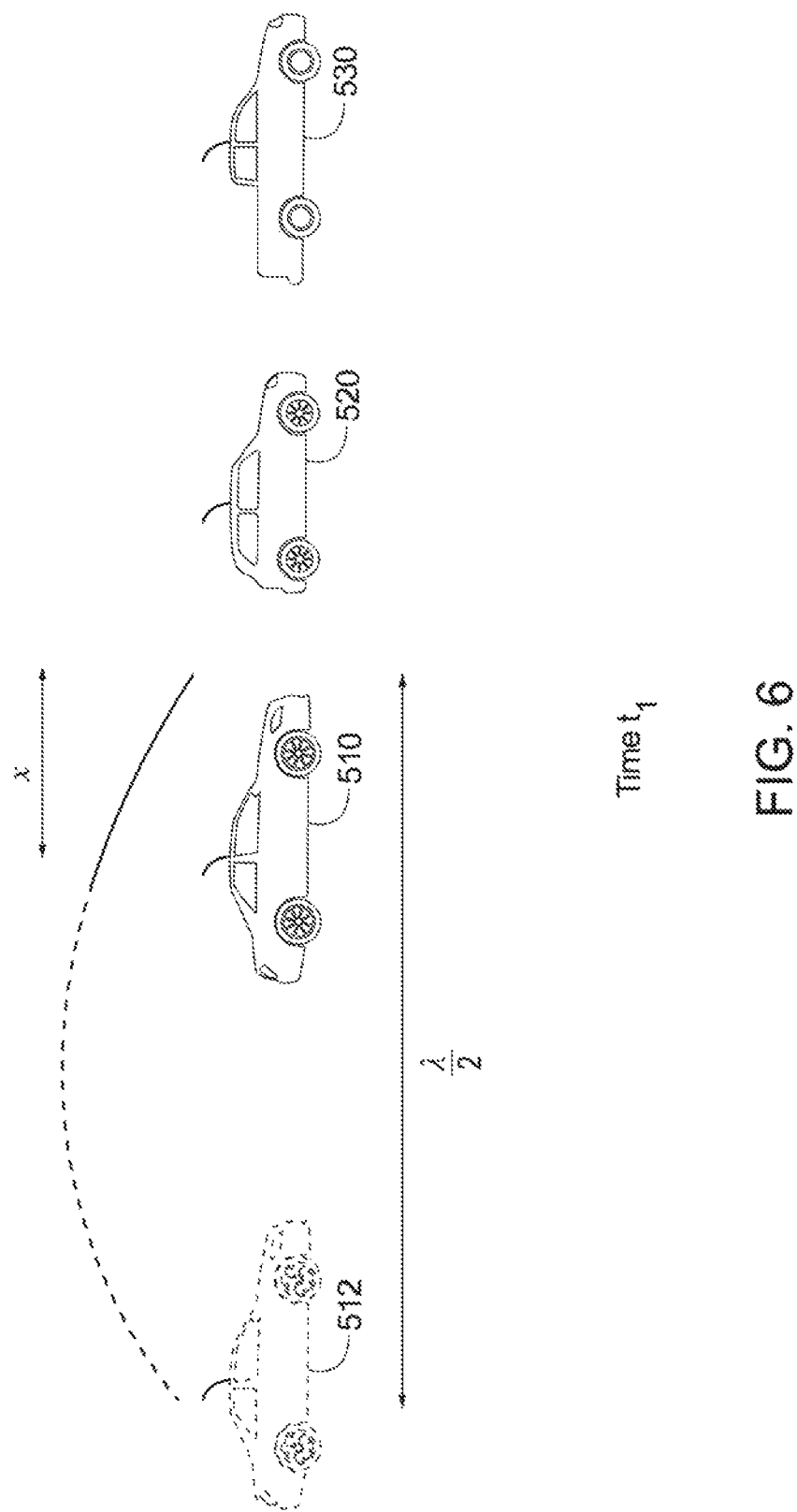
Figure 7:
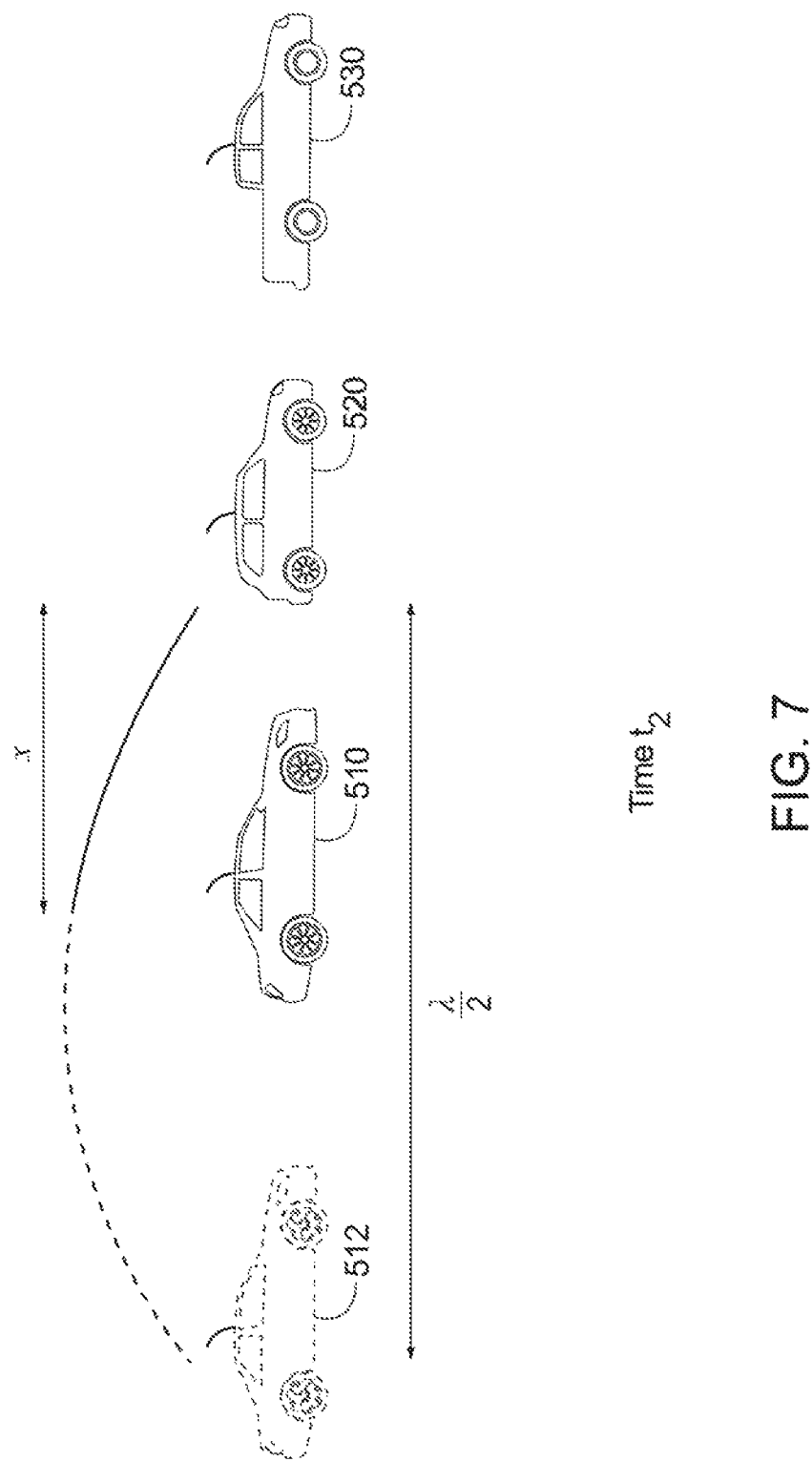

In FIG. 6, at time $t_1$, the tunable phase shifter 112 shifts the phase of the signal broadcast by the first vehicle 510 by an additional increment (e.g., 2x the incremental phase shift amount). The signal analyzer 110 may again check for a spike in the updated oscillating signal. Because no resonance has occurred, the signal analyzer 110 will not detect any spike, and thus, the tunable phase shifter 112 will shift the phase of the signal incrementally again. This is repeated in FIG. 7, at time $t_2$, and with 3× the incremental phase shift amount.

Figure 8:
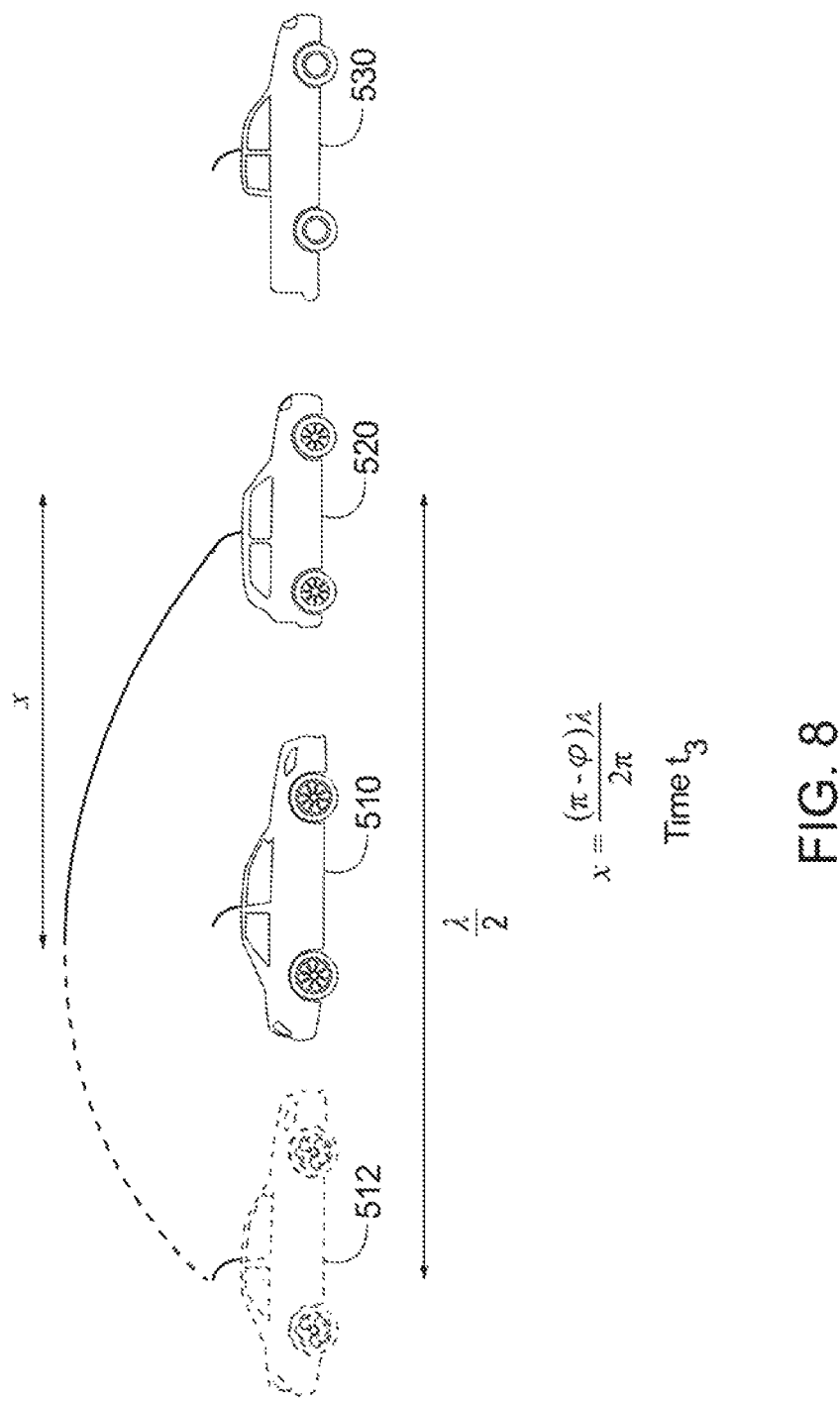

In FIG. 8, at time $t_3$, the tunable phase shifter 112 has shifted the phase of the signal broadcast by the first vehicle 510 by a multiple of the incremental phase shift amount such that the signal analyzer 110 may detect the spike in the updated oscillating signal due to the virtual, phase shifted 512 image of the first vehicle being the half wavelength distance from the second vehicle 520. Because resonance has occurred, the signal analyzer 110 will detect the spike in the updated oscillating signal, and thus, the distance estimator 126 may estimate the distance between the first vehicle and the second vehicle based on a total phase shift amount $\varphi$ and the predetermined wavelength $\lambda$ when the spike in amplitude is detected.

The system 100 for estimating the distance between vehicles may keep track of the distances between the first vehicle and multiple vehicles 520, 530 using time division multiplexing, as managed by the controller 120 or the processor 122. In other words, the oscillator 102, the tunable phase shifter 112, the transmitter 104, and the receiver 106 may operate, as described above, with respect to multiple transmissions of multiple signals over a single transmission line by using multiple time slots for respective signals. For example, for a first transmission time slot, the oscillator 102 may generate a first generated oscillating signal associated with a first phase and a first predetermined wavelength. The transmitter 104 may transmit the first generated oscillating signal, a first updated generated oscillating signal, or a first modulated signal derived from the first generated oscillating signal or the first updated generated oscillating signal as a first broadcasted signal during the first time slot. During the second transmission time slot, the transmitter 104 may transmit a second generated oscillating signal, a second updated generated oscillating signal, or a second modulated signal derived from the second generated oscillating signal or the second updated generated oscillating signal as a second broadcasted signal.

During a first receiving time slot, the receiver 106 may receive a first processed signal associated with a phase as a first received signal, wherein the first processed signal is derived by a system 150 of the second vehicle (e.g., the first RV) based on the first broadcasted signal. Similarly, during a second receiving time slot, the receiver 106 may receive a second processed signal associated with a phase as a second received signal, wherein the second processed signal is derived by a system of a third vehicle (e.g., the second RV) based on the second broadcasted signal. The summing circuit 108 may add or sum the first generated oscillating signal to the first received signal or a first demodulated signal derived from the first received signal and produce the first updated oscillating signal. Similarly, the summing circuit 108 may add or sum the second generated oscillating signal to the second received signal or a second demodulated signal derived from the second received signal and produce the second updated oscillating signal.

The signal analyzer 110 may detect the spike in amplitude associated with the first and second updated oscillating signal independently of one another and the distance estimator 126 may estimate the distance between the first vehicle 510 and the second 520 (or third 530) vehicle based on a respective total phase shift amount and the respective predetermined wavelength when the spike in amplitude is detected for the respective vehicle. In this way, the components of the system 100 for estimating the distance between vehicles may operate independently during different time slots, using time division multiplexing.

Figure 9:
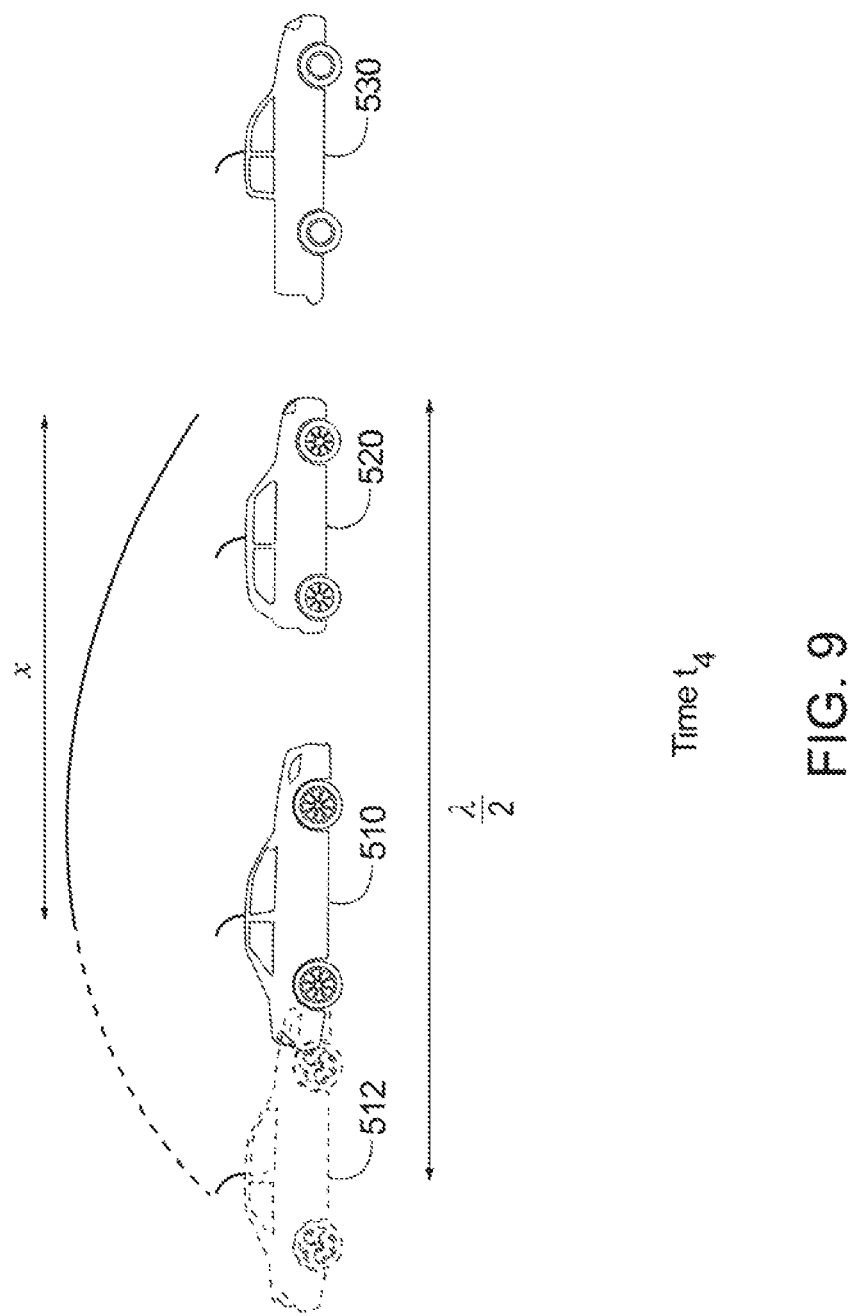
Figure 10:
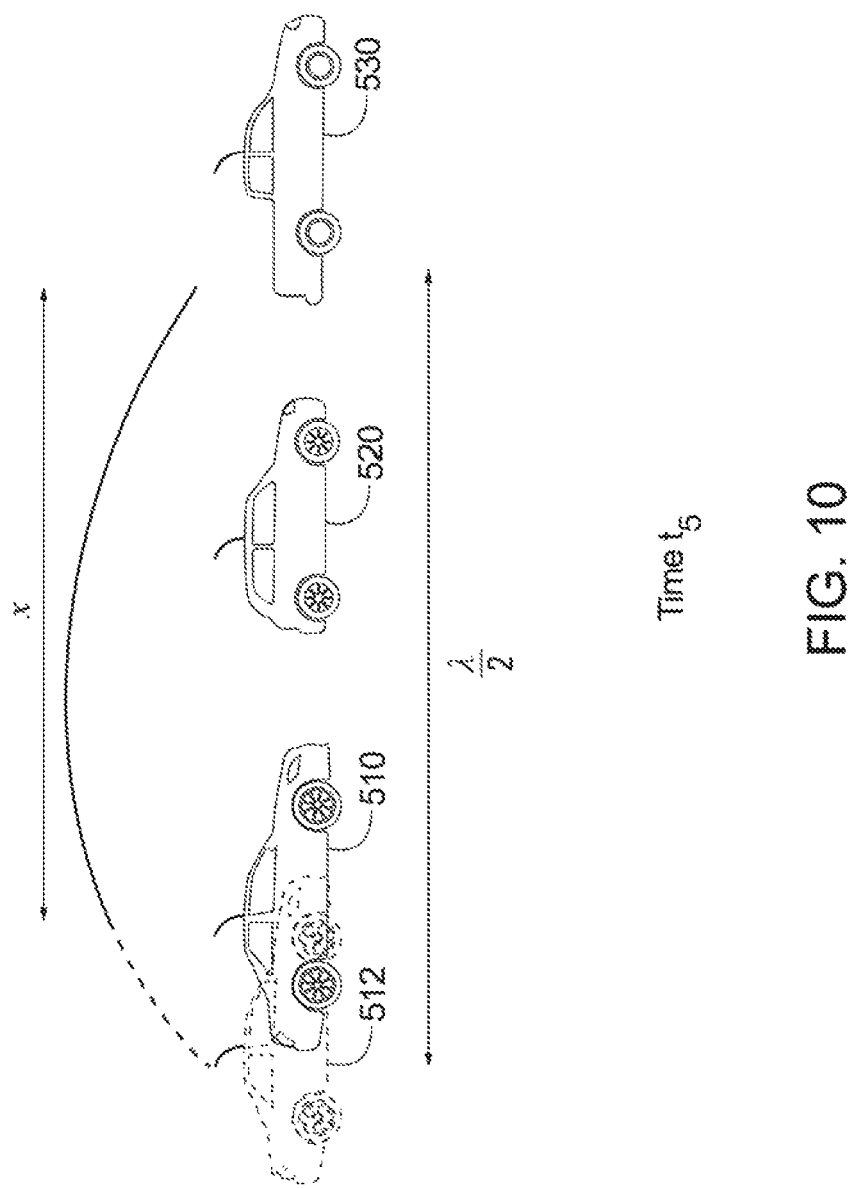

In FIG. 9, at time $t_4$, the tunable phase shifter 112 shifts the phase of the signal broadcast by the first vehicle by an additional increment (e.g., 5× the incremental phase shift amount). The signal analyzer 110 may again check for a spike in the updated oscillating signal. Because no resonance has occurred, the signal analyzer 110 will not detect any spike, and thus, the tunable phase shifter 112 will shift the phase of the signal incrementally again. This is repeated in FIG. 10, at time $t_5$, and with 6× the incremental phase shift amount.

Figure 11:
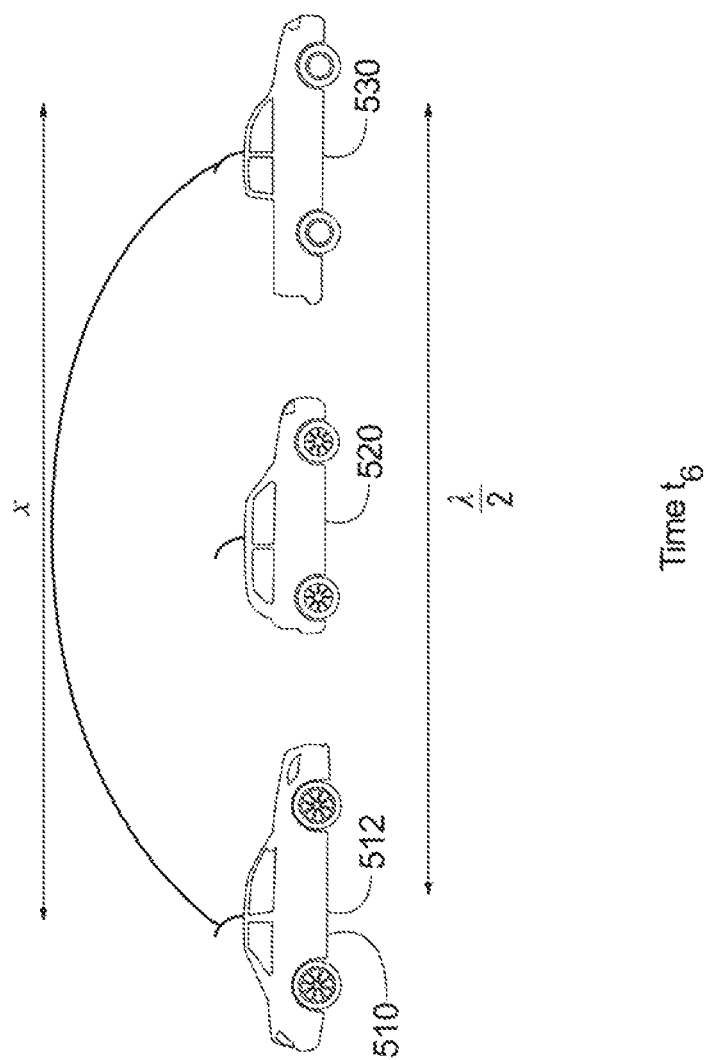

In FIG. 11, at time $t_6$, the tunable phase shifter 112 has shifted the phase of the signal broadcast by the first vehicle by a multiple of the incremental phase shift amount such that the signal analyzer 110 may detect the spike in the updated oscillating signal. In FIG. 11, the first vehicle 510 is in communication with a third vehicle 530, rather than the second vehicle 520. Because resonance has occurred, the signal analyzer 110 will detect the spike in the updated oscillating signal, and thus, the distance estimator 126 may estimate the distance between the first vehicle 510 and the third vehicle 530 based on a total phase shift amount $\varphi$ and the predetermined wavelength $\lambda$ when the spike in amplitude is detected (e.g., using the formula $x=((\pi-\varphi)\lambda)/2\pi)$.

Figure 12:
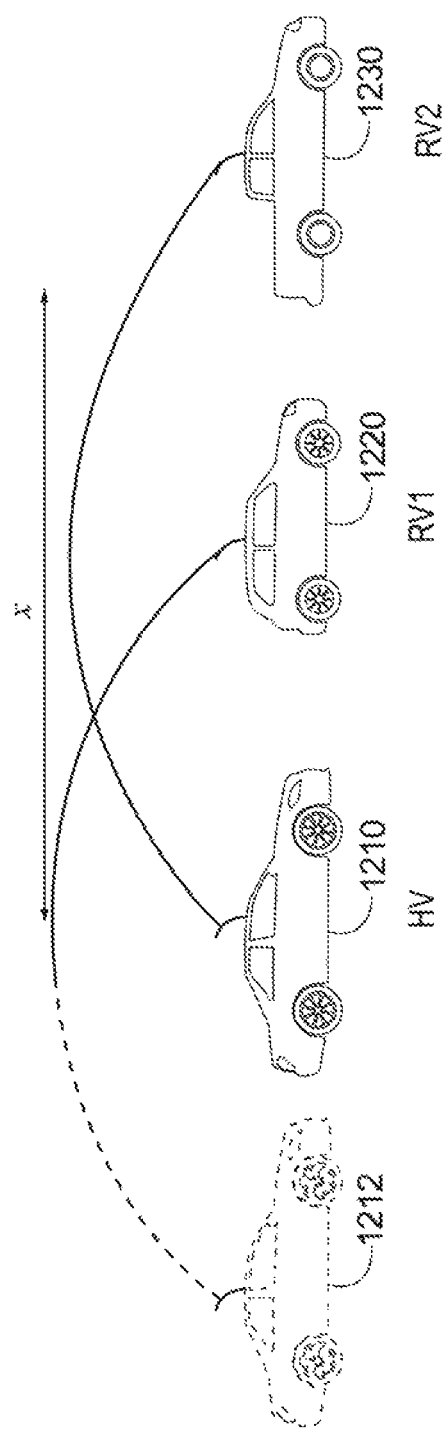
FIG. 12 is an exemplary scenario where the system for estimating a distance between vehicles of FIG. 1 may be implemented, according to one aspect, where time division multiplexing is implemented.

According to one aspect, the system 100 for estimating the distance between vehicles may operate in a second mode, which may be a tracking mode where the system tracks one or more other vehicles and maintains tracking estimates on the distance between that vehicle and the other vehicles. Similarly to the scanning mode, one of the vehicles may be the HV and the other vehicle may be the RV. In FIG. 12, it may be seen that the system 100 for estimating the distance between vehicles 1210 has established resonance with two other vehicles 1220, 1230, and using time division multiplexing, as previously discussed. Additionally, as previously noted, the distance x may be stored in the memory 124 of the system 100 for estimating the distance between vehicles in association with the respective spikes in amplitude and utilized in associated with the tracking mode. Therefore, for the second vehicle or first RV 1220, a first distance x may be stored in the memory 124 in association with this first RV and for the third vehicle or the second RV 1230, a second distance x2 may be stored in the memory 124 in association with this second RV.

Across different time periods, the relative distances x and x2 between the first vehicle (e.g., HV 1210) and the second and third vehicles (e.g., first RV 1220 and second RV 1230) may change, as the vehicles drift or as the RVs are being autonomously operated by the HV 1210. Because the relative distance x between the HV 1210 and the first RV 1220 is known, this means that the corresponding first total phase shift amount (e.g., associated with virtual, phase shifted image of the vehicle 1212) and the predetermined wavelength for the first RV are also known. The tunable phase shifter 112 may initialize the tracking mode with these known parameters (e.g., the first total phase shift amount and the first predetermined wavelength). If the signal analyzer 110 does not detect the spike in amplitude for the updated oscillating signal immediately, meaning that the first RV has drifted out of resonance, the tunable phase shifter 112 may shift the phase of the corresponding updated oscillating signal by a tracking phase shift amount within a window (e.g., which may be by both incrementing and decrementing the current phase by the tracking phase shift amount). When the signal analyzer 110 detects the spike in amplitude again, the distance estimator 126 calculates an updated estimated distance, and stores this to the memory 124 as x. This may be repeated in a corresponding fashion for x2 and the second RV 1230.

According to one aspect, the system 100 for confirming an identity of a RV among RVs associated with a HV may operate in a third mode, which may be an identification mode where the system identifies other vehicles and associates a basic safety message (BSM) received with a specific vehicle detected (e.g., by an on-board type sensor). Although it is possible to use a global positioning system (GPS) to determine the position and confirm identities of RVs with respect to the HV, there may be noise associated with the GPS signals and thus, accuracy of the positioning estimation and/or confirmation of identities of the RVs may be susceptible to error when using GPS.

Figure 13:
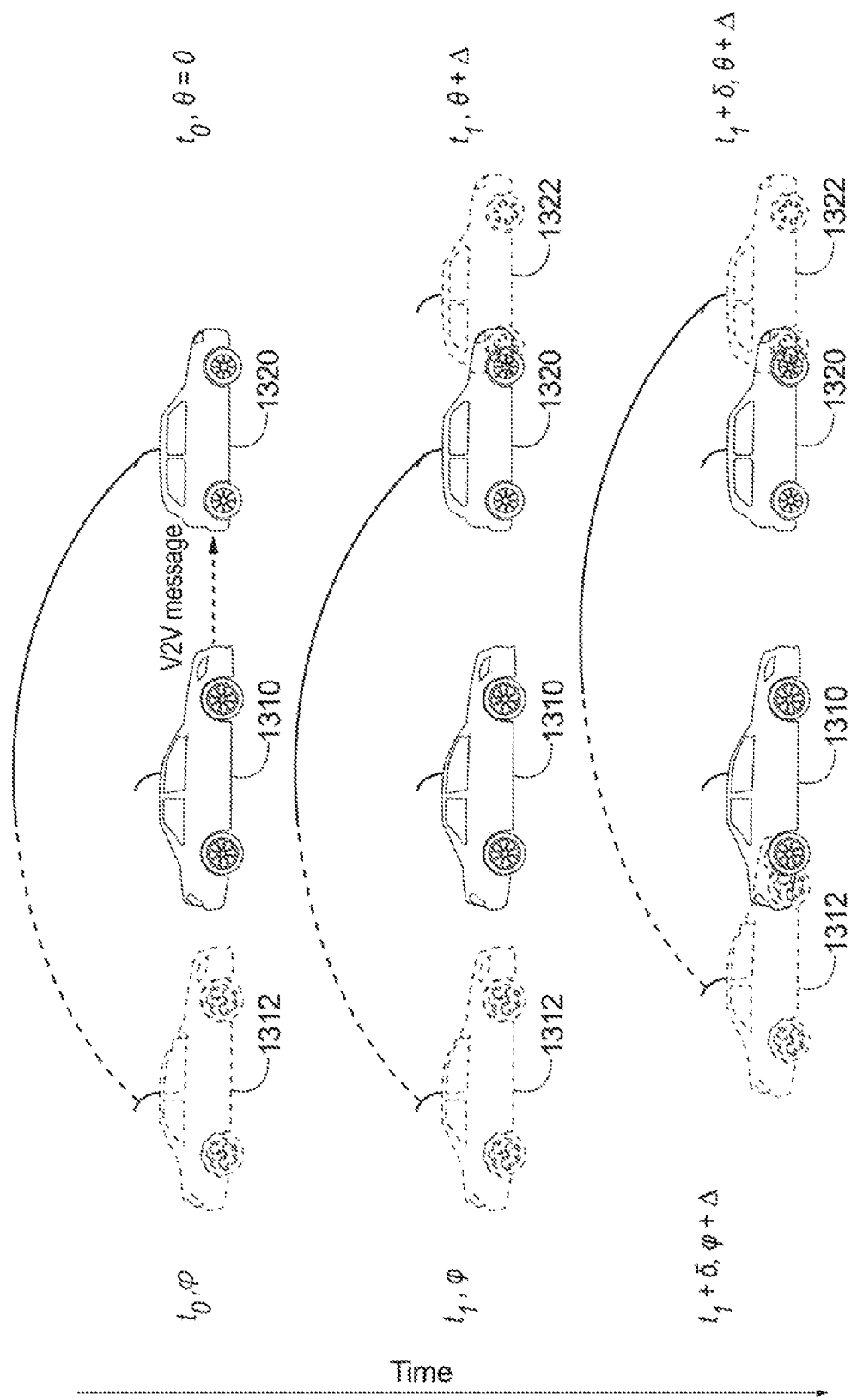
FIGS. 13-16 are exemplary scenarios where the system for confirming an identity of a remote vehicle among remote vehicles associated with a host vehicle of FIG. 1 may be implemented, according to one aspect.
Figure 14:
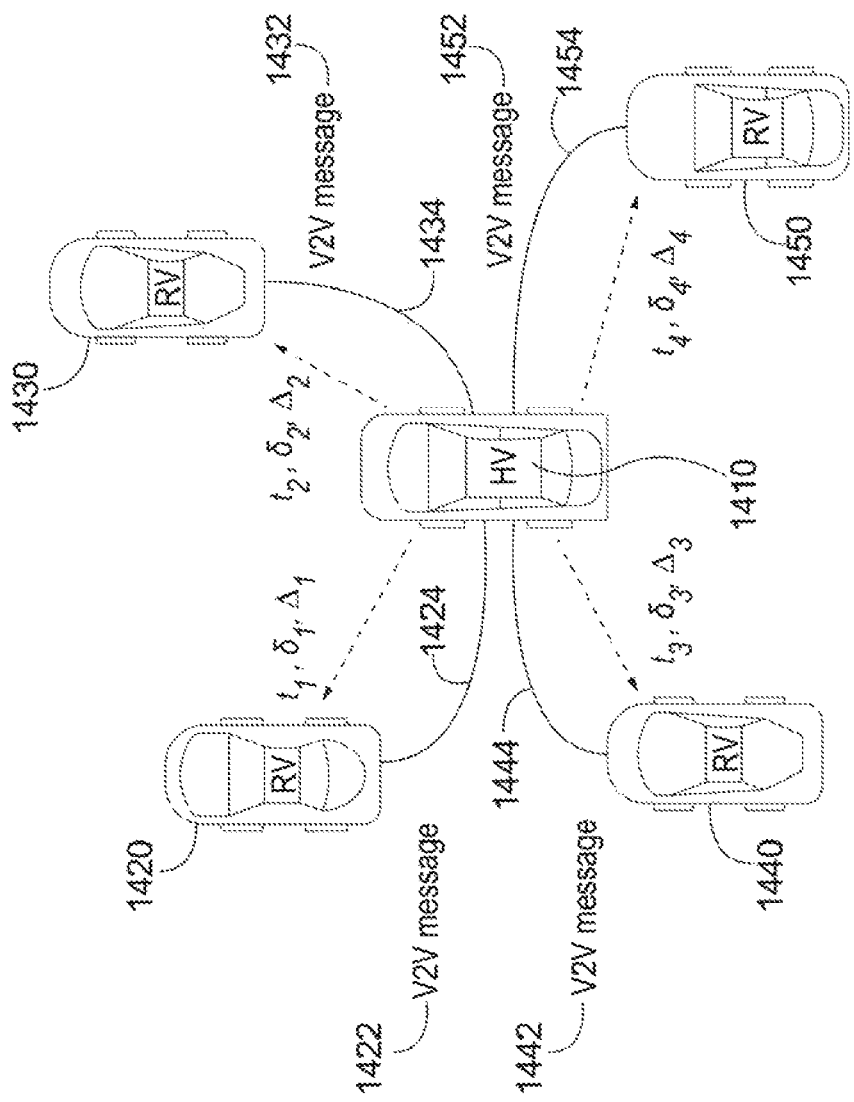
Figure 15:
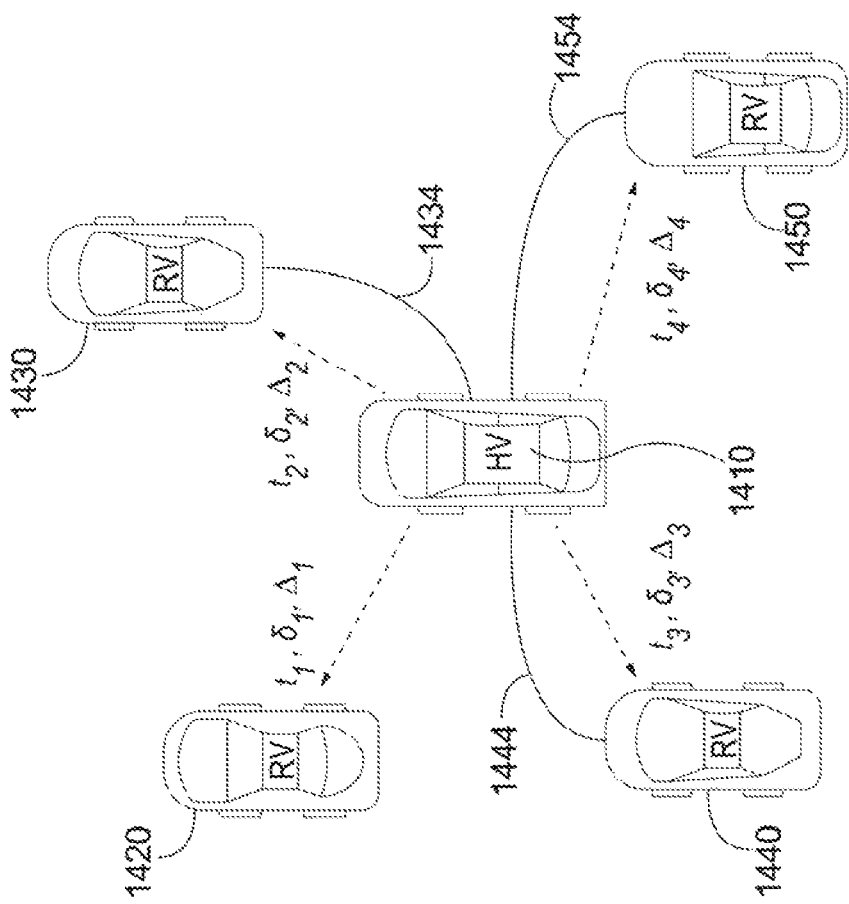

FIGS. 13-15 are exemplary scenarios where the system 100 for confirming the identity of the RV among RVs associated with the HV of FIG. 1 may be implemented, according to one aspect. As seen in FIG. 13, the system 100 for confirming the identity of the RV among RVs associated with the HV 1310 may send or transmit a V2V message as a test message commanding the tunable phase shifter 112 of the RV 1320 to (at least temporarily) break resonance (e.g., as seen at the virtual, phase shifted image of the vehicle 1312) or phase shift out of resonance with the HV 1310. For example, at time t0, the HV may use its tunable phase shifter 112 to shift the phase of the first generated oscillating signal by a resonance phase shift amount, resulting in resonance between the virtual, phase shifted 1312 image of the HV and the RV 1320. The transmitter 104 may transmit a V2V message from the HV to the RV, indicative of a time t1 at which it is desired for the RV to phase shift a test phase shift amount Δ (e.g., this may be seen at 1322). This V2V message is transmitted to the RV, and as requested, the tunable phase shifter 112 of the RV, at time t1, shifts the phase of the received broadcasted signal by the test phase shift amount Δ, at 1322. Due to this, the RV 1320 has shifted the RV 1320 out of resonance with the HV 1310, and this may be detected by the signal analyzer 110 of either the HV 1310 or the signal analyzer 160 of the RV 1320. According to one aspect, the V2V message may include instructions for realignment so that resonance is re-established, such as by having the RV shift back by −Δ or by having the HV shift the same amount as the test phase shift amount Δ, as seen at time $t_1+\delta$.

With respect to FIGS. 14-15, the oscillator 102 on the HV 1410 may generate one or more generated oscillating signals associated with one or more corresponding phases or associated with the same phase. The system 100 for estimating the distance between vehicles may determine the respective phase shifts associated with RV1 1420, RV2 1430, RV3 1440, and RV4 1450 for resonance. The vehicle identifier 128 may generate a first test message 1422 associated with the first generated oscillating signal, including a first phase shift test amount (Δ1, δ1) and a first time t1. At the first time, the tunable phase shifter 112 of either the HV or the tunable phase shifter 162 of the RV may shift the first phase of the first generated oscillating signal by the first phase shift test amount. This will result in a break in the resonance between the HV and the corresponding RV. As seen in FIG. 15, the first RV, RV1 is no longer in resonance with the HV, and thus, the signal analyzer 110 will not detect a spike in amplitude associated with the corresponding processed signal, thereby enabling the vehicle identifier 128 to identify RV1 as the first RV. Messages 1432, 1442, 1452 may also include corresponding (and different) phase shift test amounts Δ2, Δ3, Δ4, δ2, δ3, δ4 which will occur at different times t2, t3, t4, respectively.

It will be appreciated that according to some aspects, the RV may perform the shifting first, followed by the HV to re-establish resonance. In other aspects, the HV may perform the shifting first, followed by the RV. In yet other aspects, one of the HV or the RV may perform phase shifting to break resonance, followed by an opposite operation to re-establish the resonance, shown as 1424, 1434, 1444, and 1454. In FIG. 15, resonance between the HV 1410 and the RV 1420 is broken (while 1434, 1444, 1454 remain established), due to the phase shift introduced by the test message, thereby enabling the vehicle identifier 128 to identify the RV 1420.

Figure 16:
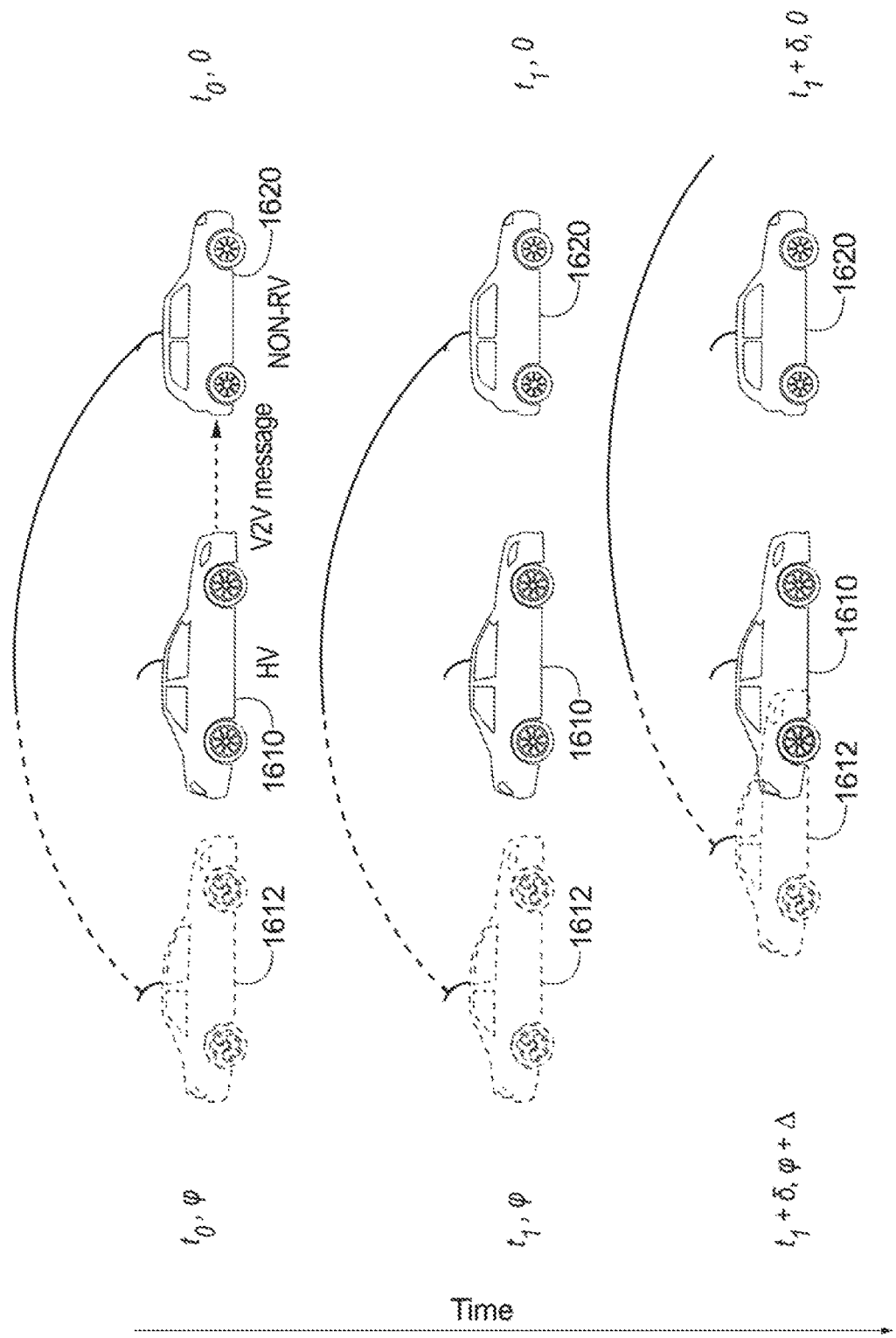

FIG. 16 is an illustration of a system 100 for confirming an identity of a non-RV. Because an object may reflect a transmitted broadcast signal back to the HV 1610, mitigation of false-positive readings may be achieved by implementing the V2V message commanding the RV 1620 to shift a test phase or indicating to the RV 1620 that a phase shift will occur. Thus, when the test signal is sent via the V2V message, the test signal includes information indicative of when a break in resonance will occur (e.g., 1612 not at the half wavelength distance from 1620), and how resonance will be re-established. In the scenario of a non-RV 1620, the V2V message will not be considered by the non-RV 1620, and thus, no re-establishing of resonance will occur. In this way, the V2V message provided by the HV 1610 enables confirmation of identities of different vehicles.

Because the system(s) 100 of FIG. 1 utilizes the principle of resonance rather than line of sight (LoS) and time of flight (ToF) to determine the distance between vehicles, an accurate range estimation may be provided when no LoS is present between vehicles because radio waves are capable of penetrating solid objects which may be obstacles between the vehicles. Similarly, resonance may also be utilized to confirm the identity of remote vehicles rather than by using radar, camera, or LIDAR sensors. Because the system 100 for confirming the identity of the RV among RVs associated with the HV may implement the signal associated with the phase shift during identification of remote vehicles, false positive identifications may be eliminated in this manner. Additionally, because the transmitters 104, 154 and receivers 106, 156 may be radio frequency (RF) transmitters and receivers, the cost associated with production may be lower than a system which implements LIDAR, for example.

It will be appreciated that the system of FIG. 1 may be implemented in conjunction with radar, camera, or LIDAR sensors to complement the operation of the system. Further, the system of FIG. 1 may act as both the system 100 for confirming the identity of the RV among RVs associated with the HV and the system 100 for estimating the distance between vehicles (i.e., the system 100 may operate in different operational modes, such as the scanning mode, the tracking mode, or the identification mode).

Figure 17:
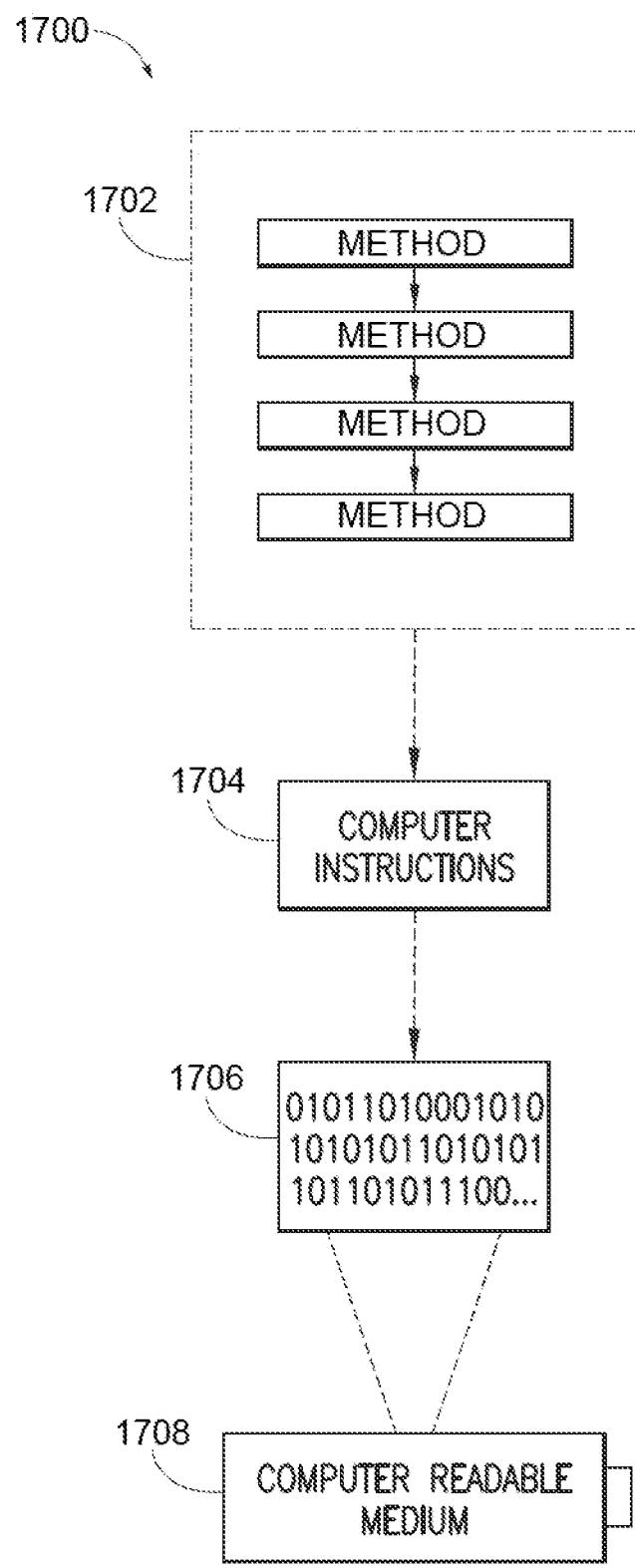
FIG. 17 is an illustration of an example computer-readable medium or computer-readable device including processor-executable instructions configured to embody one or more of the provisions set forth herein, according to one aspect.

Still another aspect involves a computer-readable medium including processor-executable instructions configured to implement one aspect of the techniques presented herein. An aspect of a computer-readable medium or a computer-readable device devised in these ways is illustrated in FIG. 17, wherein an implementation 1700 includes a computer-readable medium 1708, such as a CD-R, DVD-R, flash drive, a platter of a hard disk drive, etc., on which is encoded computer-readable data 1706. This encoded computer-readable data 1706, such as binary data including a plurality of zero's and one's as shown in 1706, in turn includes a set of processor-executable computer instructions 1704 configured to operate according to one or more of the principles set forth herein. In this implementation 1700, the processor-executable computer instructions 1704 may be configured to perform a method 1702, such as the method 200 of FIG. 2, the method 300 of FIG. 3, or the method 400 of FIG. 4. In another aspect, the processor-executable computer instructions 1704 may be configured to implement a system, such as the system 100 of FIG. 1. Many such computer-readable media may be devised by those of ordinary skill in the art that are configured to operate in accordance with the techniques presented herein.

As used in this application, the terms "component", "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, or a computer. By way of illustration, both an application running on a controller and the controller may be a component. One or more components residing within a process or thread of execution and a component may be localized on one computer or distributed between two or more computers.

Further, the claimed subject matter is implemented as a method, apparatus, or article of manufacture using standard programming or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, many modifications may be made to this configuration without departing from the scope or spirit of the claimed subject matter.

Figure 18:
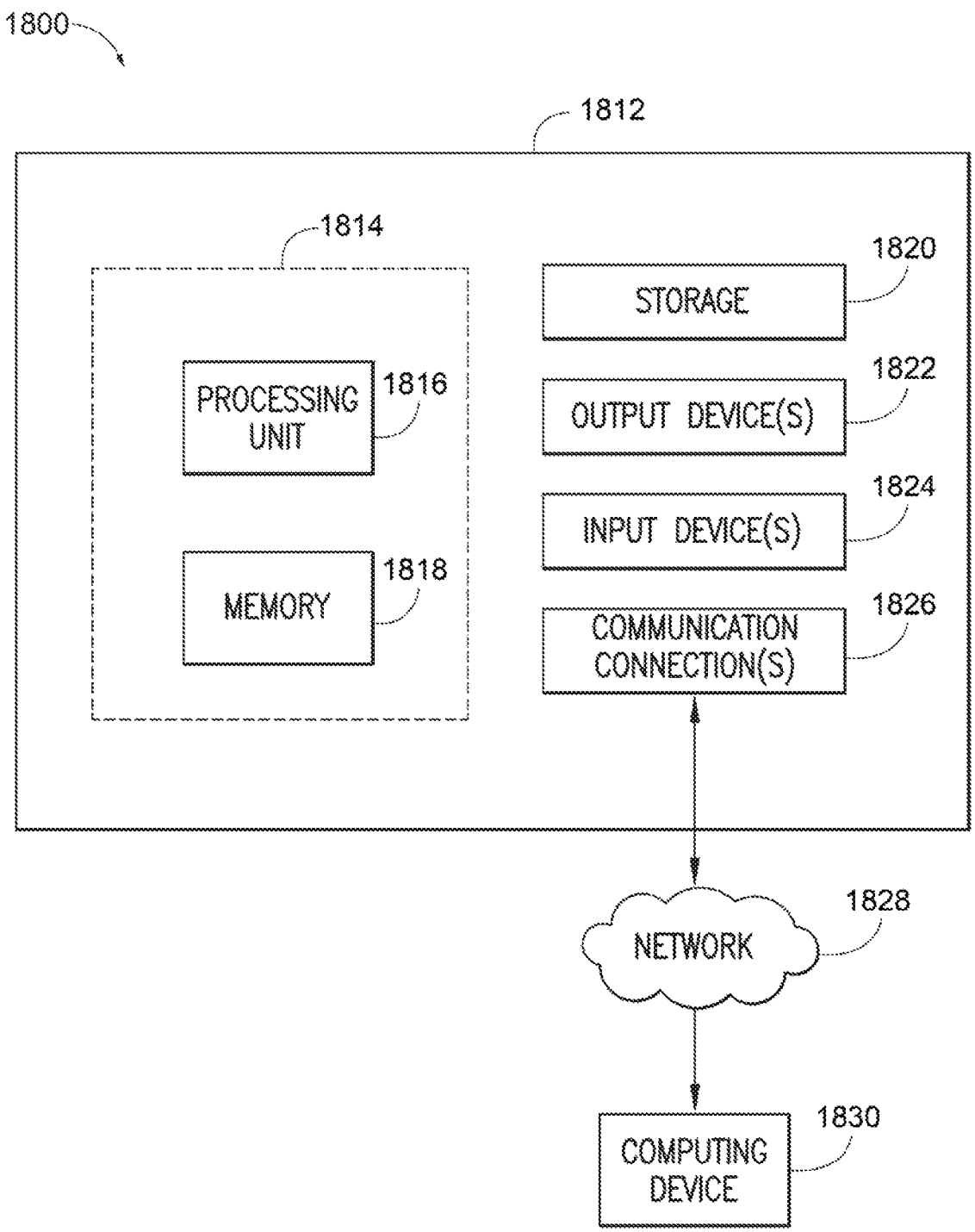
FIG. 18 is an illustration of an example computing environment where one or more of the provisions set forth herein are implemented, according to one aspect.

FIG. 18 and the following discussion provide a description of a suitable computing environment to implement aspects of one or more of the provisions set forth herein. The operating environment of FIG. 18 is merely one example of a suitable operating environment and is not intended to suggest any limitation as to the scope of use or functionality of the operating environment. Example computing devices include, but are not limited to, personal computers, server computers, hand-held or laptop devices, mobile devices, such as mobile phones, Personal Digital Assistants (PDAs), media players, and the like, multiprocessor systems, consumer electronics, mini computers, mainframe computers, distributed computing environments that include any of the above systems or devices, etc.

Generally, aspects are described in the general context of "computer readable instructions" being executed by one or more computing devices. Computer readable instructions may be distributed via computer readable media as will be discussed below. Computer readable instructions may be implemented as program modules, such as functions, objects, Application Programming Interfaces (APIs), data structures, and the like, that perform one or more tasks or implement one or more abstract data types. Typically, the functionality of the computer readable instructions are combined or distributed as desired in various environments.

FIG. 18 illustrates a system 1800 including a computing device 1812 configured to implement one aspect provided herein. In one configuration, the computing device 1812 includes at least one processing unit 1816 and memory 1818. Depending on the exact configuration and type of computing device, memory 1818 may be volatile, such as RAM, non-volatile, such as ROM, flash memory, etc., or a combination of the two. This configuration is illustrated in FIG. 18 by dashed line 1814.

In other aspects, the computing device 1812 includes additional features or functionality. For example, the computing device 1812 may include additional storage such as removable storage or non-removable storage, including, but not limited to, magnetic storage, optical storage, etc. Such additional storage is illustrated in FIG. 18 by storage 1820. In one aspect, computer readable instructions to implement one aspect provided herein are in storage 1820. Storage 1820 may store other computer readable instructions to implement an operating system, an application program, etc. Computer readable instructions may be loaded in memory 1818 for execution by processing unit 1816, for example.

The term "computer readable media" as used herein includes computer storage media. Computer storage media includes volatile and nonvolatile, removable and non-removable media implemented in any method or technology for storage of information such as computer readable instructions or other data. Memory 1818 and storage 1820 are examples of computer storage media. Computer storage media includes, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which may be used to store the desired information and which may be accessed by the computing device 1812. Any such computer storage media is part of the computing device 1812.

The term "computer readable media" includes communication media. Communication media typically embodies computer readable instructions or other data in a "modulated data signal" such as a carrier wave or other transport mechanism and includes any information delivery media. The term "modulated data signal" includes a signal that has one or more of its characteristics set or changed in such a manner as to encode information in the signal.

The computing device 1812 includes input device(s) 1824 such as keyboard, mouse, pen, voice input device, touch input device, infrared cameras, video input devices, or any other input device. Output device(s) 1822 such as one or more displays, speakers, printers, or any other output device may be included with the computing device 1812. Input device(s) 1824 and output device(s) 1822 may be connected to the computing device 1812 via a wired connection, wireless connection, or any combination thereof. In one aspect, an input device or an output device from another computing device may be used as input device(s) 1824 or output device(s) 1822 for the computing device 1812. The computing device 1812 may include communication connection(s) 1826 to facilitate communications with one or more other devices 1830, such as through network 1828, for example.

Although the subject matter has been described in language specific to structural features or methodological acts, it is to be understood that the subject matter of the appended claims is not necessarily limited to the specific features or acts described above. Rather, the specific features and acts described above are disclosed as example aspects.

Various operations of aspects are provided herein. The order in which one or more or all of the operations are described should not be construed as to imply that these operations are necessarily order dependent. Alternative ordering will be appreciated based on this description. Further, not all operations may necessarily be present in each aspect provided herein.

As used in this application, "or" is intended to mean an inclusive "or" rather than an exclusive "or". Further, an inclusive "or" may include any combination thereof (e.g., A, B, or any combination thereof). In addition, "a" and "an" as used in this application are generally construed to mean "one or more" unless specified otherwise or clear from context to be directed to a singular form. Additionally, at least one of A and B and/or the like generally means A or B or both A and B. Further, to the extent that "includes", "having", "has", "with", or variants thereof are used in either the detailed description or the claims, such terms are intended to be inclusive in a manner similar to the term "comprising".

Further, unless specified otherwise, "first", "second", or the like are not intended to imply a temporal aspect, a spatial aspect, an ordering, etc. Rather, such terms are merely used as identifiers, names, etc. for features, elements, items, etc. For example, a first channel and a second channel generally correspond to channel A and channel B or two different or two identical channels or the same channel. Additionally, "comprising", "comprises", "including", "includes", or the like generally means comprising or including, but not limited to.

It will be appreciated that various of the above-disclosed and other features and functions, or alternatives or varieties thereof, may be desirably combined into many other different systems or applications. Also that various presently unforeseen or unanticipated alternatives, modifications, variations or improvements therein may be subsequently made by those skilled in the art which are also intended to be encompassed by the following claims.

The invention claimed is:

1. A system for estimating a distance between vehicles based on radio frequency (RF), comprising:
   an oscillator equipped on a first vehicle generating a generated oscillating signal associated with a first phase and a predetermined wavelength;
   a transmitter transmitting an updated generated oscillating signal or a modulated signal derived from the updated generated oscillating signal, wherein the updated generated oscillating signal or the modulated signal is transmitted as a broadcast signal;
   a receiver receiving a signal associated with a second phase as a received signal, wherein the signal received by the receiver is derived by a system of a second vehicle based on the broadcasted signal;
   a summing circuit adding the generated oscillating signal to the received signal or a demodulated signal derived from the received signal and producing the updated generated oscillating signal;
   a signal analyzer detecting a spike in amplitude associated with the updated generated oscillating signal;
   a tunable phase shifter shifting the first phase of the generated oscillating signal by an incremental phase shift amount when no spike in amplitude is detected; and
   a distance estimator, implemented via a processor, estimating the distance between the first vehicle and the second vehicle based on a total phase shift amount and the predetermined wavelength when the spike in amplitude is detected,
wherein the predetermined wavelength is set as double a maximum vehicle to vehicle (V2V) communication range distance between the first vehicle and the second vehicle and the signal analyzer detects the spike in amplitude of the updated generated oscillating signal when a phase shifted image of the first vehicle is one half the predetermined wavelength distance away from the second vehicle.

2. The system for estimating the distance between vehicles of claim 1, wherein the transmitter modulates the generated oscillating signal to generate the modulated signal.

3. The system for estimating the distance between vehicles of claim 2, wherein the transmitter modulates a frequency, an amplitude, or a phase of the generated oscillating signal to generate the modulated signal.

4. The system for estimating the distance between vehicles of claim 1, wherein the predetermined wavelength is set based on a vehicle to vehicle (V2V) communication range distance between the first vehicle and the second vehicle or set as double the V2V communication range distance.

5. The system for estimating the distance between vehicles of claim 4, wherein the distance estimator calculates the distance x between the first vehicle and the second vehicle as $x=((\pi-\varphi)\lambda)/2\pi)$, wherein $\lambda$ is the predetermined wavelength set as double the V2V communication range distance between the first vehicle and the second vehicle, and wherein $\varphi$ is the total phase shift amount resulting in the spike in amplitude of the updated generated oscillating signal.

6. The system for estimating the distance between vehicles of claim 1, wherein the transmitter or receiver include an omni-directional radio frequency (RF) antenna or a rotating directional RF antenna.

7. The system for estimating the distance between vehicles of claim 1, wherein the oscillator generates the generated oscillating signal at a frequency less than 5 MHz and wherein the modulated signal has a frequency greater than 2 GHz.

8. The system for estimating the distance between vehicles of claim 1, wherein the first vehicle is a host vehicle and the second vehicle is a remote vehicle and the host vehicle directs an aspect of autonomous driving for the remote vehicle.

9. The system for estimating the distance between vehicles of claim 1, wherein the second vehicle is a host vehicle and the first vehicle is a remote vehicle and the host vehicle directs an aspect of autonomous driving for the remote vehicle.

10. The system for estimating the distance between vehicles of claim 1, wherein the transmitter and receiver are mounted at a center area of the first vehicle.

11. The system for estimating the distance between vehicles of claim 1, wherein the signal analyzer detects the spike in amplitude based on an amplitude of the updated generated oscillating signal exceeding a threshold amplitude.

12. The system for estimating the distance between vehicles of claim 1, wherein the tunable phase shifter shifts the first phase of the generated oscillating signal by decrementing the first phase by the incremental phase shift amount.

13. The system for estimating the distance between vehicles of claim 1, wherein the signal analyzer detects the spike in amplitude based on an occurrence of resonance.

14. The system for estimating the distance between vehicles of claim 1, comprising a memory storing the distance between the first vehicle and the second vehicle when the spike in amplitude is detected.

15. A computer-implemented method for estimating a distance between vehicles based on radio frequency (RF), comprising:
generating, at a first vehicle, a generated oscillating signal associated with a first phase and a predetermined wavelength;
transmitting an updated generated oscillating signal or a modulated signal derived from the updated generated oscillating signal, wherein the updated generated oscillating signal or the modulated signal is transmitted as a broadcast signal;
receiving a signal associated with a second phase as a received signal, wherein the signal associated with the second phase is derived by a system of a second vehicle based on the broadcasted signal;
summing the generated oscillating signal with the received signal or a demodulated signal derived from the received signal and producing the updated generated oscillating signal;
detecting a spike in amplitude associated with the updated generated oscillating signal;
shifting the first phase of the generated oscillating signal by an incremental phase shift amount when no spike in amplitude is detected; and
estimating, via a processor, the distance between the first vehicle and the second vehicle based on a total phase shift amount and the predetermined wavelength when the spike in amplitude is detected,
wherein the predetermined wavelength is set as double a maximum vehicle to vehicle (V2V) communication range distance between the first vehicle and the second vehicle and the signal analyzer detects the spike in amplitude of the updated generated oscillating signal when a phase shifted image of the first vehicle is one half the predetermined wavelength distance away from the second vehicle.

16. The method for estimating the distance between vehicles of claim 15, comprising modulating the generated oscillating signal to generate the modulated signal.

17. The method for estimating the distance between vehicles of claim 15, comprising setting the predetermined wavelength based on a vehicle to vehicle (V2V) communication range distance between the first vehicle and the second vehicle or double the V2V communication range distance.

18. The method for estimating the distance between vehicles of claim 15, comprising calculating the distance x between the first vehicle and the second vehicle as $x=((\pi-\varphi)\lambda)/2\pi)$, wherein $\lambda$ is the predetermined wavelength set as double the V2V communication range distance between the first vehicle and the second vehicle, and wherein $\varphi$ is the total phase shift amount resulting in the spike in amplitude of the updated generated oscillating signal.

* * * * *